US012669595B2

(12) United States Patent　　(10) Patent No.:　US 12,669,595 B2

Na et al.　　(45) Date of Patent:　Jun. 30, 2026

(54) PROBE CAPABLE OF SELF-INSPECTION, ULTRASONIC IMAGING SYSTEM HAVING THE SAME, AND METHOD OF CONTROLLING THE SAME

(71) Applicant: SAMSUNG MEDISON CO., LTD., Hongcheon-gun (KR)

(72) Inventors: Minsoo Na, Seoul (KR); Hwanseung Yu, Seoul (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 194 days.

(21) Appl. No.: 18/587,352

(22) Filed: Feb. 26, 2024

(65) Prior Publication Data

US 2025/0123380 A1　Apr. 17, 2025

(30) Foreign Application Priority Data

Oct. 12, 2023　(KR) ........................ 10-2023-0136057

(51) Int. Cl.
*G01S 7/52* (2006.01)
*A61B 8/00* (2006.01)

(52) U.S. Cl.
CPC ........ *G01S 7/52004* (2013.01); *A61B 8/4472* (2013.01); *A61B 8/54* (2013.01); *A61B 8/58* (2013.01)

(58) Field of Classification Search
CPC .. G01S 7/52004; G01S 7/5208; G01S 7/5205; A61B 8/4472; A61B 8/54;

(Continued)

(56) References Cited

U.S. PATENT DOCUMENTS 6,211,815 B1 * 4/2001 Richey ................. H02M 3/285
342/21
11,619,729 B2 4/2023 Hyeon
(Continued)

FOREIGN PATENT DOCUMENTS

EP 　　　3692924 A1　12/2020
JP 　2007-244580 A　　9/2007
(Continued)

OTHER PUBLICATIONS

The Extended European Search Report dated Jul. 17, 2024 issued in European Patent Application No. 24159230.2.
(Continued)

*Primary Examiner* — Lee E Rodak
*Assistant Examiner* — Zannatul Ferdous
(74) *Attorney, Agent, or Firm* — Morgan Lewis & Bockius LLP

(57) ABSTRACT

Disclosed is a probe including a first transmitter provided to generate a first transmission signal, a second transmitter provided to generate a second transmission signal, a receiver provided to receive the first transmission signal generated from the first transmitter or the second transmission signal generated from the second transmitter, a signal attenuator provided to attenuate the first transmission signal or the second transmission signal, a first switching element provided to transmit the first transmission signal to the signal attenuator or to transmit the second transmission signal transmitted through the signal attenuator to the receiver, a second switching element provided to transmit the second transmission signal to the signal attenuator or to transmit the first transmission signal transmitted through the signal attenuator to the receiver, a first node provided between a first transducer and the first switching element, a second node provided between a second transducer and the second (Continued)

switching element, and a controller configured to control the first switching element and the second switching element, wherein the signal attenuator is connected between the first node and the second node.

20 Claims, 24 Drawing Sheets

(58) Field of Classification Search
CPC ......... A61B 8/58; A61B 8/4438; A61B 8/464; A61B 8/4444; A61B 8/4477
See application file for complete search history.

(56) References Cited

U.S. PATENT DOCUMENTS

| | | | |
|---|---|---|---|
| 2010/0286527 | A1 | 11/2010 | Cannon et al. |
| 2015/0293214 | A1 | 10/2015 | Cannon et al. |
| 2017/0067858 | A1 | 3/2017 | Segall |
| 2017/0105703 | A1 | 4/2017 | Han et al. |
| 2020/0256969 | A1* | 8/2020 | Hyeon ................ G01S 7/52087 |
| 2022/0071598 | A1* | 3/2022 | Hwang ................... A61B 8/483 |
| 2022/0202522 | A1* | 6/2022 | Czupi ....................... A61B 8/58 |
| 2023/0240652 | A1 | 8/2023 | Jin et al. |

FOREIGN PATENT DOCUMENTS

| | | | |
|---|---|---|---|
| JP | 2007-319176 | A | 12/2007 |
| JP | 2008-018109 | A | 1/2008 |
| JP | 5346496 | B2 | 11/2013 |
| KR | 10-2017-0043864 | A | 4/2017 |
| KR | 10-2019-0022265 | A | 3/2019 |
| KR | 10-2019-0049378 | A | 5/2019 |

OTHER PUBLICATIONS

European Communication dated Oct. 22, 2025 issued in European Patent Application No. 24159230.2.

* cited by examiner

Figure 9:
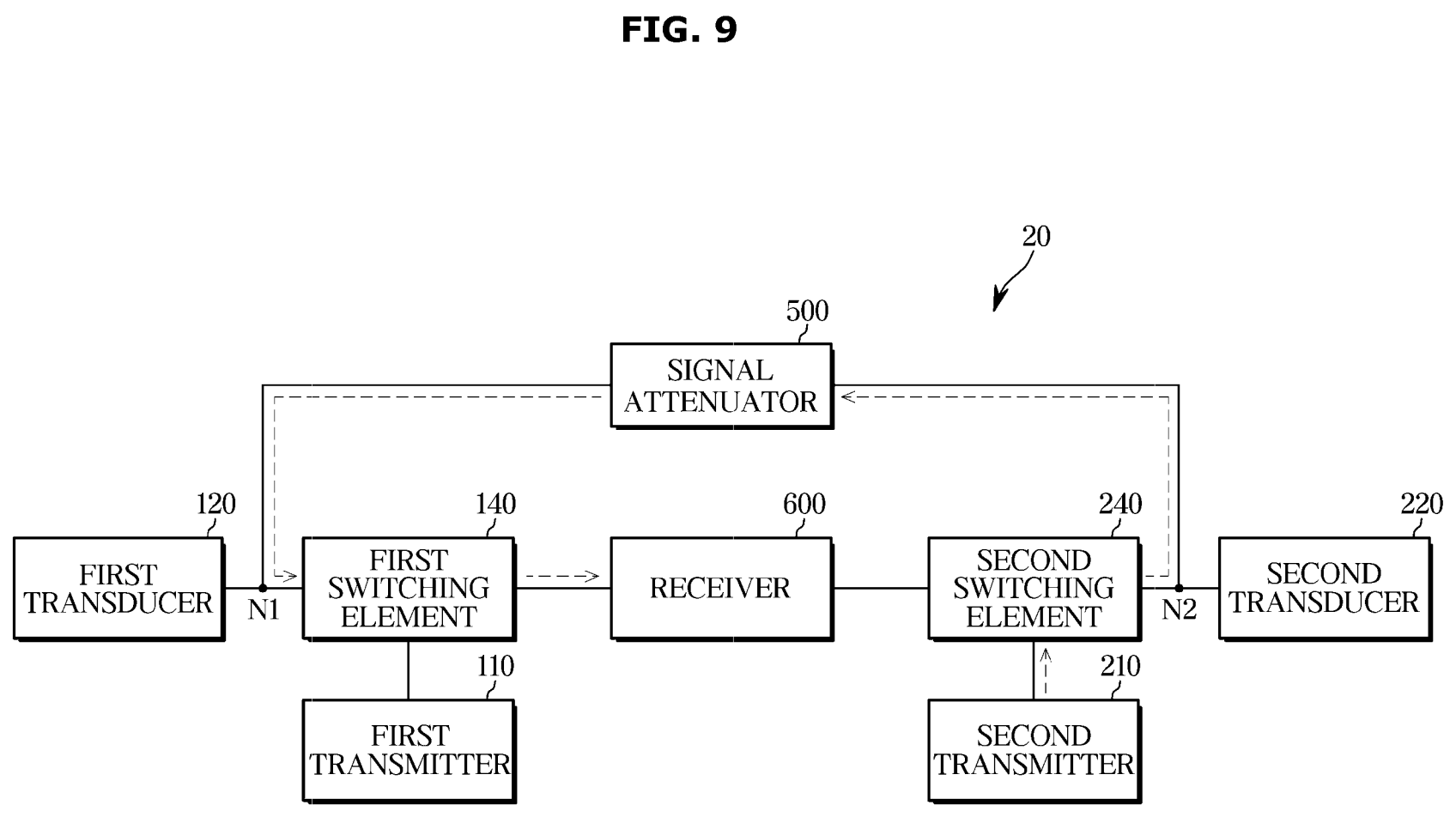

SECOND TRANSDUCER 220

SECOND SWITCHING ELEMENT 240

SECOND TRANSMITTER 210

N2

SIGNAL ATTENUATOR 500

RECEIVER 600

FIRST SWITCHING ELEMENT 140

FIRST TRANSMITTER 110

N1

FIRST TRANSDUCER 120

FIG. 12

START

INPUT SECOND INSPECTION MODE — 1310

TURN ON FIRST SWITCHING ELEMENT AND TURN OFF SECOND SWITCHING ELEMENT — 1320

OUTPUT SECOND TRANSMISSION SIGNAL FROM SECOND TRANSMITTER — 1330

DETECT SECOND WAVEFORM INFORMATION OF SECOND TRANSMISSION SIGNAL FROM FIRST RECEIVER — 1340

DETERMINE SECOND OPERATING STATES OF SECOND TRANSMITTER AND FIRST RECEIVER — 1350

END

PROBE CAPABLE OF SELF-INSPECTION, ULTRASONIC IMAGING SYSTEM HAVING THE SAME, AND METHOD OF CONTROLLING THE SAME

CROSS-REFERENCE TO RELATED APPLICATION(S)

This application is based on and claims priority under 35 U.S.C. § 119 to Korean Patent Application No. 10-2023-0136057, filed on Oct. 12, 2023, in the Korean Intellectual Property Office, the disclosure of which is incorporated by reference herein in its entirety.

BACKGROUND

1. Field

The disclosure relates to a probe capable of self-inspection, an ultrasonic imaging system having the same, and a method of controlling the same.

2. Description of the Related Art

Recently, in a medical field, various medical imaging devices have been widely used to image and obtain information about biological tissues of a human body for the purpose of early diagnosis of various diseases or surgery. Representative examples of such medical imaging devices may include ultrasonic imaging devices, CT devices, and MRI devices.

An ultrasonic imaging device is a device that emits an ultrasonic signal generated from a transducer of a probe to an object, and non-invasively obtains at least one image of a region inside the object (e.g., soft tissue or blood flow) by receiving information from the signal reflected from the object. In particular, an ultrasonic imaging device is used for medical purposes such as observing the inside of an object, detecting foreign substances, and measuring injury. Such an ultrasonic imaging device is widely used along with other imaging diagnostic devices because the ultrasonic imaging device has higher stability than an imaging device using an X-ray, may display images in real time, and is safe because there is no radiation exposure.

An image of a target region as described above may be obtained through a probe connected to the main body by a wire, but in order to obtain the image of the target region regardless of time and place, an ultrasonic probe to be operated wirelessly is required.

When operated wirelessly, the probe needs be able to perform most of the operations performed in the main body, but because there are many spatial limitations in design, research and development to overcome these limitations have recently been actively conducted.

In addition, in the case of wireless ultrasonic imaging devices, many different types of dual head structures configured on opposite sides are being adopted in consideration of user convenience.

SUMMARY

It is an aspect of the disclosure to provide a probe capable of self-inspection, an ultrasonic imaging system having the same, and a method of controlling the same.

Additional aspects of the disclosure will be set forth in part in the description which follows and, in part, will be obvious from the description, or may be learned by practice of the disclosure.

In accordance with an aspect of the disclosure, a probe includes a first transmitter provided to generate a first transmission signal, a second transmitter provided to generate a second transmission signal, a receiver provided to receive the first transmission signal generated from the first transmitter or the second transmission signal generated from the second transmitter, a signal attenuator provided to attenuate the first transmission signal or the second transmission signal, a first switching element provided to transmit the first transmission signal to the signal attenuator or to transmit the second transmission signal transmitted through the signal attenuator to the receiver, a second switching element provided to transmit the second transmission signal to the signal attenuator or to transmit the first transmission signal transmitted through the signal attenuator to the receiver, a first node provided between a first transducer and the first switching element, a second node provided between a second transducer and the second switching element, and a controller configured to control the first switching element and the second switching element, wherein the signal attenuator is connected between the first node and the second node.

In accordance with another aspect of the disclosure, a method of controlling a probe includes generating a first transmission signal from a first transmitter, generating a second transmission signal from a second transmitter, attenuating the first transmission signal or the second transmission signal, receiving the first transmission signal generated from the first transmitter or the second transmission signal generated from the second transmitter through a receiver, transmitting, based on an operation of the first switching element, the first transmission signal to the signal attenuator, or the second transmission signal transmitted through the signal attenuator to the receiver, and transmitting, based on an operation of the second switching element, the second transmission signal to the signal attenuator, or the first transmission signal transmitted through the signal attenuator to the receiver.

In accordance with another aspect of the disclosure, an ultrasonic imaging system includes a probe, and an ultrasonic imaging device provided to communicate wirelessly with the probe, wherein the probe includes a first transmitter provided to generate a first transmission signal, a second transmitter provided to generate a second transmission signal, a receiver provided to receive the first transmission signal generated from the first transmitter or the second transmission signal generated from the second transmitter, a signal attenuator provided to attenuate the first transmission signal or the second transmission signal, a first switching element provided to transmit the first transmission signal to the signal attenuator or to transmit the second transmission signal transmitted through the signal attenuator to the receiver, a second switching element provided to transmit the second transmission signal to the signal attenuator or to transmit the first transmission signal transmitted through the signal attenuator to the receiver, a first node provided between a first transducer and the first switching element, a second node provided between a second transducer and the second switching element, and a controller configured to control the first switching element and the second switching element, and wherein the signal attenuator is connected between the first node and the second node.

According to the disclosure, as a structure for disposing a signal attenuator is optimized, there is an effect that more accurate inspection is possible by being free from a parasitic capacitance caused by a switching element.

In addition, as signal attenuators are not disposed on a first head side and a second head side, respectively, and a single signal attenuator connecting both the head sides is disposed, there is an effect that the number of circuit elements can be significantly reduced.

Technical tasks and effects to be achieved in this document are not limited to the technical tasks described above, and other technical tasks and effects not mentioned will be clearly understood by those skilled in the art from the description below.

BRIEF DESCRIPTION OF THE DRAWINGS

These and/or other aspects of the disclosure will become apparent and more readily appreciated from the following description of the embodiments, taken in conjunction with the accompanying drawings of which:

FIGS. 1A and 1B are block diagrams illustrating configurations of an ultrasonic imaging system according to an embodiment;

FIG. 4 is a block diagram illustrating briefly a circuit structure of the probe of the ultrasonic imaging system according to an embodiment;

FIG. 9 is a diagram illustrating a control operation of the controller on the circuit diagram of the probe of the ultrasonic imaging system according to another embodiment;

FIG. 12 is a block diagram illustrating in more detail the circuit structure of the probe of the ultrasonic imaging system according to another embodiment;

DETAILED DESCRIPTION

Figure 1A:
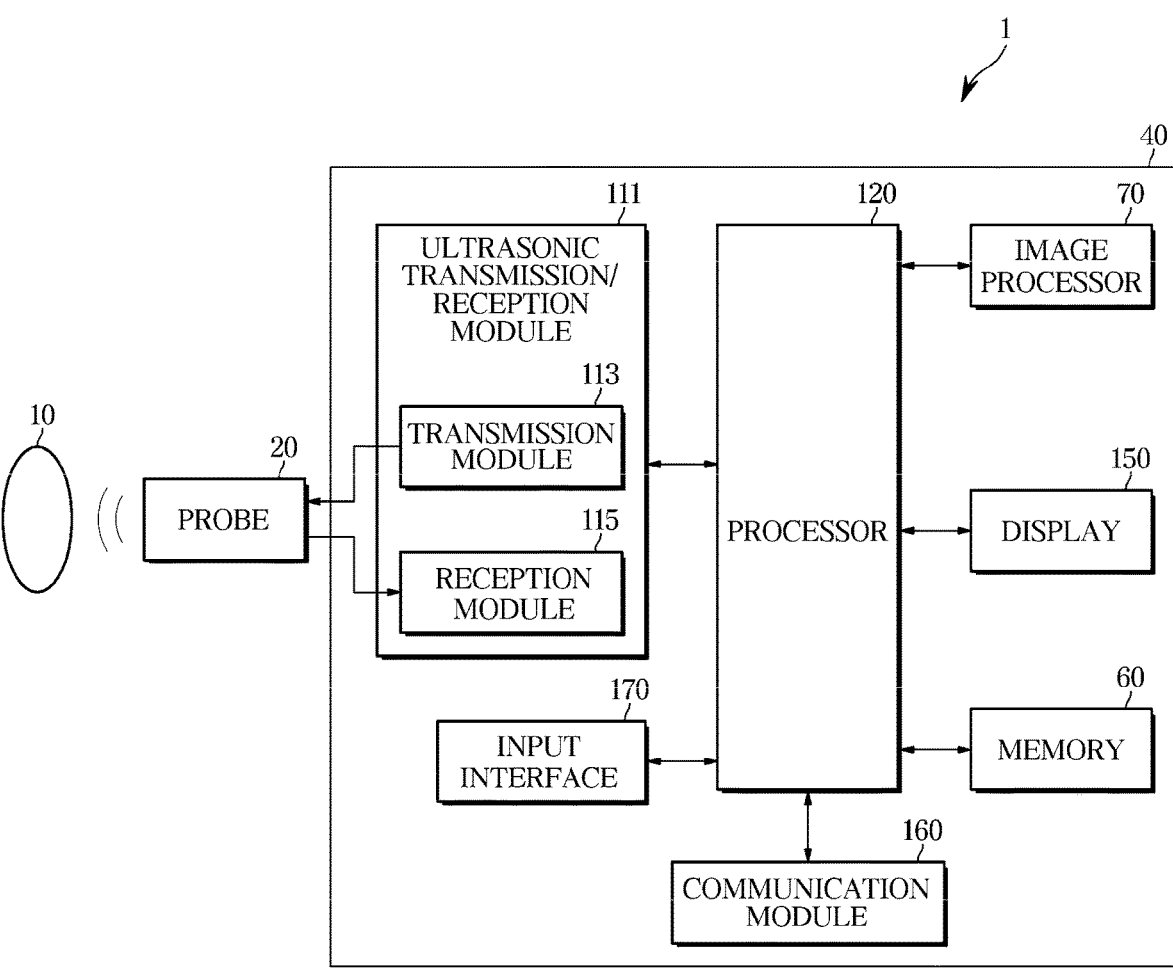

The various embodiments of the disclosure and the terms used herein are not intended to limit the technical features described in the disclosure to specific embodiments, and should be understood to include various changes, equivalents, or replacements of the embodiments.

In connection with the description of the drawings, similar reference numbers may be used for similar or related components.

The singular form of a noun corresponding to an item may include a single item or a plurality of items, unless the relevant context clearly indicates otherwise.

In this disclosure, each of phrases such as "A or B," "at least one of A and B," "at least one of A or B," "A, B or C," "at least one of A, B and C," and "at least one of A, B, or C" may include any one of the items listed together in the corresponding one of the phrases, or all possible combinations thereof.

The term "and/or" includes any combination of a plurality of related components or any one of a plurality of related components.

The terms such as "first," "second," "primary," and "secondary" may simply be used to distinguish a given component from other corresponding components, and do not limit the corresponding components in any other respect (e.g., importance or order).

The terms "front surface," "rear surface," "upper surface," "lower surface," "side surface," "left side," "right side," "upper portion," "lower portion," and the like used in the disclosure are defined with reference to the drawings, and the shape and position of each component are not limited by these terms.

The terms "comprises," "has," and the like are intended to indicate that there are features, numbers, steps, operations, components, parts, or combinations thereof described in the disclosure, and do not exclude the presence or addition of one or more other features, numbers, steps, operations, components, parts, or combinations thereof.

When any component is referred to as being "connected," "coupled," "supported," or "in contact" with another component, this includes a case in which the components are indirectly connected, coupled, supported, or in contact with each other through a third component as well as directly connected, coupled, supported, or in contact with each other.

When any component is referred to as being located "on" or "over" another component, this includes not only a case in which any component is in contact with another component but also a case in which another component is present between the two components.

Hereinafter, an ultrasonic device according to various embodiments will be described in detail with reference to the accompanying drawings. When described with reference to the attached drawings, similar reference numbers may be assigned to identical or corresponding components and redundant description thereof may be omitted.

In the disclosure, images may include a medical image obtained by a medical imaging device, such as a magnetic resonance imaging (MRI) device, a computed tomography (CT) device, an ultrasonic imaging device, and an x-ray imaging device.

In the disclosure, an 'object', which is subject to photography, may include a person, animal, or part thereof. For example, the object may include a part of a human body (organ, etc.) or a phantom.

Throughout the disclosure, an 'ultrasonic image' refers to an image of an object that has been processed based on an ultrasonic signal transmitted to and reflected from the object.

Figure 1B:
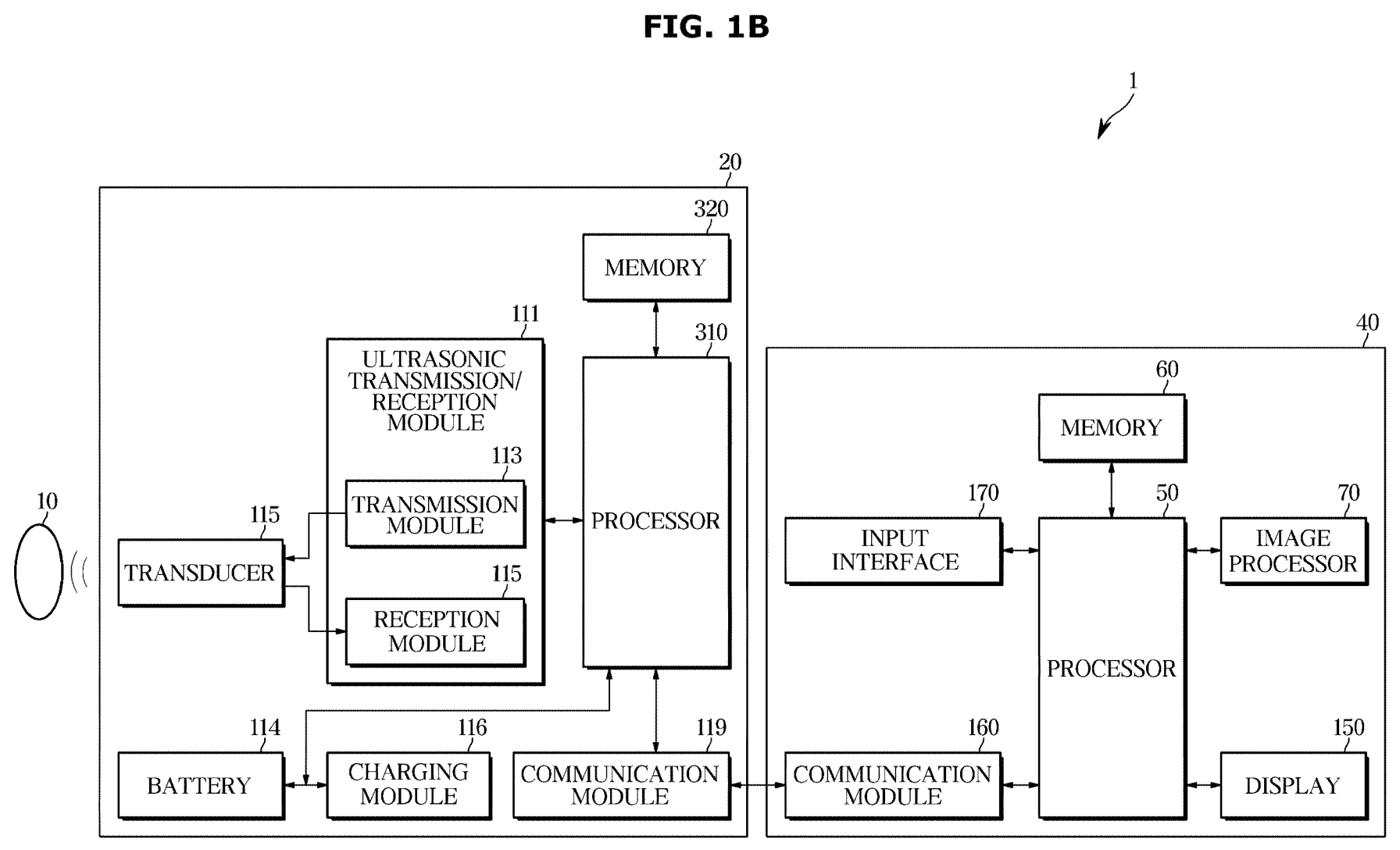

FIGS. 1A and 1B are block diagrams illustrating configurations of an ultrasonic imaging system according to an embodiment.

Referring to FIGS. 1A and 1B, an ultrasonic imaging system 1 may include a probe 20 and an ultrasonic imaging device 40.

The ultrasonic imaging device 40 may be implemented not only in a cart type but also in a portable type. A portable ultrasonic imaging device may include, for example, a smart phone, laptop computer, PDA, tablet PC, etc., which include a probe and an application, but is not limited thereto.

The probe 20 may include a wired probe connected to the ultrasonic imaging device 40 by wire to communicate with the ultrasonic imaging device 40 by wire, a wireless probe wirelessly connected to the ultrasonic imaging device 40 to communicate wirelessly with the ultrasonic imaging device 40, and/or a hybrid probe by wire or wirelessly connected to the ultrasonic imaging device 40 to communicate by wire or wirelessly with the ultrasonic imaging device 40.

According to various embodiments, as illustrated in FIG. 1A, the ultrasonic imaging device 40 may include an ultrasonic transmission/reception module 111, or as Illustrated in FIG. 1B, the probe 20 may include the ultrasonic transmission/reception module 111. According to various embodiments, both the ultrasonic imaging device 40 and the probe 20 may also include the ultrasonic transmission/reception module 111.

According to various embodiments, the probe 20 may further include an image processor 70, a display 150, and/or an input interface 170.

Accordingly, the descriptions of the ultrasonic transmission/reception module 111, the image processor 70, the display 150, and/or the input interface 170 included in the ultrasonic imaging device 40 may also be applied to the ultrasonic transmission/reception module 111, the image processor 70, the display 150, and/or the input interface 170 included in the probe 20.

FIG. 1A illustrates a control block diagram of the ultrasonic imaging system 1 in a case in which the probe 20 is a wired probe or a hybrid probe.

The probe 20 may include a plurality of transducers. The plurality of transducers may transmit an ultrasonic signal to an object 10 in response to a transmission signal applied from a transmission module 113. The plurality of transducers may form a received signal by receiving the ultrasonic signal (echo signal) reflected from the object 10. The probe 20 may be implemented as an integrated type with the ultrasonic imaging device 40, or may be implemented as a separate type connected to the ultrasonic imaging device 40 by wire. The ultrasonic imaging device 40 may be connected to the one or more probes 20 depending on the implementation type.

In the case in which the probe 20 is a wired probe or a hybrid probe, the probe 20 may include a cable and a connector capable of being connected to a connector of the ultrasonic imaging device 40.

The probe 20 according to an embodiment may be implemented as a two-dimensional probe. In a case in which the probe 20 is implemented as a two-dimensional probe, the plurality of transducers included in the probe 20 may be arranged in two dimensions to form a two-dimensional transducer array.

For example, the two-dimensional transducer array may have a form in which a plurality of sub-arrays including the plurality of transducers arranged in a first direction is arranged in a second direction different from the first direction.

In addition, in the case in which the probe 20 is implemented as a two-dimensional probe, the ultrasonic transmission/reception module 111 may include an analog beamformer and a digital beamformer. Alternatively, the two-dimensional probe may include one or both of the analog beamformer and the digital beamformer depending on the implementation type.

A processor 50 controls the transmission module 113 to form a transmission signal to be applied to each of the transducers 117 in consideration of positions and focused points of the plurality of transducers included in the probe 20.

The processor 50 may control a reception module 115 to generate ultrasonic data by converting reception signals received from the probe 20 to analog to digital and summing up the digitally converted reception signals in consideration of the positions and focused points of the plurality of transducers.

In the case in which the probe 20 is implemented as a two-dimensional probe, the processor 50 may calculate a time delay value for digital beamforming for each sub-array for each of the plurality of sub-arrays included in the two-dimensional transducer array. The processor 50 may also calculate a time delay value for analog beamforming for each of the transducers included in one of the plurality of sub-arrays. The processor 50 may control the analog beamformer and the digital beamformer to form a transmission signal to be applied to each of the plurality of transducers depending on the time delay values for analog beamforming and the time delay values for digital beamforming. The processor 50 may also control the analog beamformer to sum up the signals received from the plurality of transducers for each sub-array depending on the time delay values for analog beamforming. The processor 50 may also control the ultrasonic transmission/reception module 112 to convert the summed signal for each sub-array to analog to digital. The processor 50 may also control the digital beamformer to generate ultrasonic data by summing up the digitally converted signals depending on the time delay values for digital beamforming.

The image processor 70 generates an ultrasonic image using the generated ultrasonic data.

The display 150 may display the generated ultrasonic image and a variety of information processed by the ultrasonic imaging device 40 and/or the probe 20. The probe 20 and/or the ultrasonic imaging device 40 may include the one or more displays 150 depending on the implementation type. The display 150 may also include a touch panel or a touch screen.

The processor 50 may control the overall operation of the ultrasonic imaging device 40 and signal flow between internal components of the ultrasonic imaging device 40. The processor 50 may perform or control various operations or functions of the ultrasonic imaging device 40 by executing programs or instructions stored in a memory 60. The processor 50 may also control an operation of the ultrasonic imaging device 40 by receiving a control signal from the input interface 170 or an external device.

The ultrasonic imaging device 40 may include a communication module 160, and may be connected to an external device (e.g., the probe 20, a server, medical device, portable device (a smart phone, tablet PC, wearable device, etc.)) through the communication module 160.

The communication module 160 may include one or more components that enable communication with the external device, and may include, for example, at least one of a short-range communication module, a wired communication module, and a wireless communication module.

The communication module 160 may receive a control signal and data from the external device, and may transmit the received control signal to the processor 50 to enable the processor 50 to control the ultrasonic imaging device 40 depending on the received control signal.

Alternatively, the processor 50 may transmit a control signal to the external device through the communication module 160 to control the external device depending on the control signal of the processor.

For example, the external device may process data within the external device depending on the control signal of the processor received through the communication module.

A program capable of controlling the ultrasonic imaging device 40 may be installed in the external device, and this program may include instructions for performing some or all of the operations of the processor 50.

The program may be pre-installed on the external device, or a user of the external device may download and install the program from a server providing an application. The server providing the application may include a recording medium in which the program is stored.

The memory 60 may store various data or programs for driving and controlling the ultrasonic imaging device 40, inputted and outputted ultrasonic data, ultrasonic images, etc.

The input interface 170 may receive user input for controlling the ultrasonic imaging device 40. For example, the user input may include, but is not limited to, input of manipulating a button, a keypad, a mouse, a trackball, a jog switch, a knob, and the like, input of touching a touch pad or touch screen, voice input, motion input, biometric information input (e.g., iris recognition, fingerprint recognition, etc.), and the like.

FIG. 1B illustrates a control block diagram of the ultrasonic imaging system 100 in the case in which the probe 20 is a wireless probe or a hybrid probe.

According to various embodiments, the ultrasonic imaging device 40 illustrated in FIG. 1B may be replaced with the ultrasonic imaging device 40 described with reference to FIG. 1A.

According to various embodiments, the probe 20 illustrated in FIG. 1A may be replaced with the probe 20 to be described with reference to FIG. 1B.

The probe 20 may include the transmission module 113, a battery 114, the transducer 117, a charging module 116, the reception module 115, a processor 310, and a communication module 119. Although FIG. 1B illustrates that the probe 20 includes both the transmission module 113 and the reception module 115, the probe 20 may include only part of a configuration of the transmission module 113 and the reception module 115 depending on the implementation type, and the part of the configuration of the transmission module 113 and the reception module 115 may be included in the ultrasonic imaging device 40. Alternatively, the probe 20 may further include the image processor 70.

The transducer 117 may include a plurality of transducers. The plurality of transducers may transmit an ultrasonic signal to the object 10 in response to the transmission signal applied from the transmission module 113. The plurality of transducers may receive the ultrasonic signal reflected from the object 10 to form a reception signal.

The charging module 116 may charge the battery 114. The charging module 116 may receive electric power from the outside. The charging module 116 may receive electric power wirelessly. However, the disclosure is not limited thereto, and the charging module 116 may receive electric power by wire. The charging module 116 may transfer the received electric power to the battery 114.

The processor 310 controls the transmission module 113 to form a transmission signal to be applied to each of the plurality of transducers in consideration of the positions and focused points of the plurality of transducers.

The processor 310 controls the reception module 115 to generate ultrasonic data by converting reception signals received from the transducer 117 to analog to digital and summing up the digitally converted reception signals in consideration of the positions and focused points of the plurality of transducers. Alternatively, in a case in which the probe 20 includes the image processor 70, the probe 20 may generate an ultrasonic image using the generated ultrasonic data.

In the case in which the probe 20 is implemented as a two-dimensional probe, the processor 310 may calculate a time delay value for digital beamforming for each sub-array for each of the plurality of sub-arrays included in the two-dimensional transducer array. The processor 310 may also calculate a time delay value for analog beamforming for each of the transducers included in one of the plurality of sub-arrays. The processor 310 may control the analog beamformer and the digital beamformer to form a transmission signal to be applied to each of the plurality of transducers depending on the time delay values for analog beamforming and the time delay values for digital beamforming. The processor 310 may also control the analog beamformer to sum up the signals received from the plurality of transducers for each sub-array depending on the time delay values for analog beamforming. The processor 310 may also control the ultrasonic transmission/reception module 111 to convert the summed signal for each sub-array to analog to digital. The processor 310 may also control the digital beamformer to generate ultrasonic data by summing up the digitally converted signals depending on the time delay values for digital beamforming.

The processor 310 may control the overall operation of the probe 20 and the signal flow between internal components of the probe 20. The processor 310 may perform or control the various operations or functions of the probe 20 by executing programs or instructions stored in a memory 320. The processor 310 may also control the operation of the probe 20 by receiving the control signal from the input interface 170 of the probe 20 or an external device (e.g., the ultrasonic imaging device 40).

The communication module 119 may wirelessly transmit the generated ultrasonic data or ultrasonic images to the ultrasonic imaging device 40 through a wireless network. The communication module 119 may also receive control signals and data from the ultrasonic imaging device 40.

The ultrasonic imaging device 40 may receive the ultrasonic data or ultrasonic images from the probe 20.

In an embodiment, in a case in which the probe 20 includes the image processor 70 capable of generating an ultrasonic image using the ultrasonic data, the probe 20 may transmit the ultrasonic data and/or the ultrasonic images generated by the image processor 70 to the ultrasonic imaging device 40.

In an embodiment, in a case in which the probe 20 does not include the image processor 70 capable of generating an ultrasonic image using the ultrasonic data, the probe 20 may transmit the ultrasonic data to the ultrasonic imaging device 40. The ultrasonic data may include ultrasonic raw data, and the ultrasonic image may refer to ultrasonic image data.

The ultrasonic imaging device 40 may include the processor 50, the image processor 70, the display 150, the memory 60, the communication module 160, and the input interface 170.

The image processor 70 generates an ultrasonic image using the ultrasonic data received from the probe 20.

The display 150 may display an ultrasonic image received from the probe 20, an ultrasonic image generated by processing the ultrasonic data received from the probe 20, and a variety of information processed by the ultrasonic imaging system 1. The ultrasonic imaging device 40 may include the one or more displays 150 depending on the implementation type. The display 150 may include a touch panel or a touch screen.

The processor 50 may control the overall operation of the ultrasonic imaging device 40 and the signal flow between the internal components of the ultrasonic imaging device 40. The processor 50 may perform or control the various operations or functions of the ultrasonic imaging device 40 by executing the programs or applications stored in a memory 60. The processor 50 may also control the operation of the ultrasonic imaging device 40 by receiving the control signal from the input interface 170 or an external device.

The ultrasonic imaging device 40 may include the communication module 160, and may be connected to an external device (e.g., the probe 20, a server, medical device, portable device (a smart phone, tablet PC, wearable device, etc.)) through the communication module 160.

The communication module 160 may include one or more components that enable communication with the external device, and may include, for example, at least one of a short-range communication module, a wired communication module, and a wireless communication module.

The communication module 160 of the ultrasonic imaging device 40 and the communication module 119 of the probe 20 may communicate using a network or a short-range wireless communication method. For example, the communication module 160 of the ultrasonic imaging device 40 and the communication module 119 of the probe 20 may communicate using any one of wireless LAN, Wi-Fi, Bluetooth, ZigBee, Wi-Fi Direct (WFD), Infrared Data Association (IrDA), Bluetooth Low Energy (BLE), Near Field Communication (NFC), Wireless Broadband Internet (WiBro), World Interoperability for Microwave Access (WIMAX), Shared Wireless Access Protocol (SWAP), Wireless Gigabit Alliance (WiGig), RF communication, a wireless data communication method including 60 GHz millimeter wave (mm wave) short-range communication, etc.

To this end, the communication module 160 of the ultrasonic imaging device 40 and the communication module 119 of the probe 20 may include at least one of a wireless LAN communication module, a Wi-Fi communication module, a Bluetooth communication module, a ZigBee communication module, a Wi-Fi Direct (WFD) communication module, an Infrared Data Association (IrDA) communication module, a Bluetooth Low Energy (BLE) communication module, a Near Field Communication (NFC) module, a Wireless Broadband Internet (WiBro) communication module, a World Interoperability for Microwave Access (WiMAX) communication module, a Shared Wireless Access Protocol (SWAP) communication module, a Wireless Gigabit Alliance (WiGig) communication module, a RF communication module, and a 60 GHz millimeter wave (mm wave) short-range communication module.

In an embodiment, the probe 20 may transmit device information (e.g., ID information) of the probe 20 using a first communication method (e.g., BLE), may be wirelessly paired with the ultrasonic imaging device 40, and may transmit ultrasonic data and/or ultrasonic images to the paired ultrasonic imaging device 40.

The device information of the probe 20 may include a variety of information related to a serial number, model name, and battery state of the probe 20.

The ultrasonic imaging device 40 may receive the device information (e.g., ID information) of the probe 20 from the probe 20 using the first communication method (e.g., BLE), may be wirelessly paired with the probe 20, may transmit an activation signal to the paired probe 20, and may receive the ultrasonic data and/or ultrasonic images from the probe 20. In this case, the activation signal may include a signal for controlling the operation of the probe 20.

In an embodiment, the probe 20 may transmit the device information (e.g., ID information) of the probe 20 using the first communication method (e.g., BLE), may be wirelessly paired with the ultrasonic imaging device 40, and may transmit the ultrasonic data and/or ultrasonic images to the ultrasonic imaging device 40 paired by the first communication method using a second communication method (e.g., 60 GHz millimeter wave and Wi-Fi).

The ultrasonic imaging device 40 may receive the device information (e.g., ID information) of the probe 20 from the probe 20 using the first communication method (e.g., BLE), may be wirelessly paired with the probe 20, may transmit the activation signal to the paired probe 20, and may receive the ultrasonic data and/or ultrasonic images from the probe 20 using the second communication method (e.g., 60 GHz millimeter wave and Wi-Fi).

According to various embodiments, the first communication method used to pair the probe 20 and the ultrasonic imaging device 40 with each other may have a lower frequency band than a frequency band of the second communication method used by the probe 20 to transmit the ultrasonic data and/or ultrasonic images to the ultrasonic imaging device 40.

The display 150 of the ultrasonic imaging device 40 may display UIs indicating the device information of the probe 20. For example, the display 150 may display UIs, which indicate identification information of the ultrasonic probe 20, a pairing method indicating the pairing method with the probe 20, a data communication state between the probe 20 and the ultrasonic imaging device 40, a method of performing data communication with the ultrasonic imaging device 40, and the battery state of the probe 20.

In a case in which the probe 20 includes the display 150, the display 150 of the probe 20 may display UIs indicating the device information of the probe 20. For example, the display 150 may display UIs, which indicate the identification information of the wireless probe 20, the pairing method indicating the pairing method with the probe 20, the data communication state between the probe 20 and the ultrasonic imaging device 40, the method of performing data communication with the ultrasonic imaging device 40, and the battery state of the probe 20.

The communication module 160 may also receive a control signal and data from an external device and transmit the received control signal to the processor 50 so that the processor 50 controls the ultrasonic imaging device 40 depending on the received control signal.

Alternatively, the processor 50 may transmit a control signal to an external device through the communication module 160 to control the external device depending on the control signal of the processor 50.

For example, the external device may process data of the external device depending on the control signal of the processor 50 received through the communication module.

A program capable of controlling the ultrasonic imaging device 40 may be installed in the external device, and this program may include instructions for performing some or all of the operations of the processor 50.

The program may be pre-installed on the external device, or the user of the external device may download and install the program from the server providing the application. The server providing the application may include the recording medium in which the program is stored.

The memory 60 may store various data or programs for driving and controlling the ultrasonic imaging device 40, inputted and outputted ultrasonic data, ultrasonic images, etc.

Examples of the ultrasonic imaging system 1 according to an embodiment of the disclosure will be described later through FIGS. 2A, 2B, 2C, and 2D.

Figure 2A:
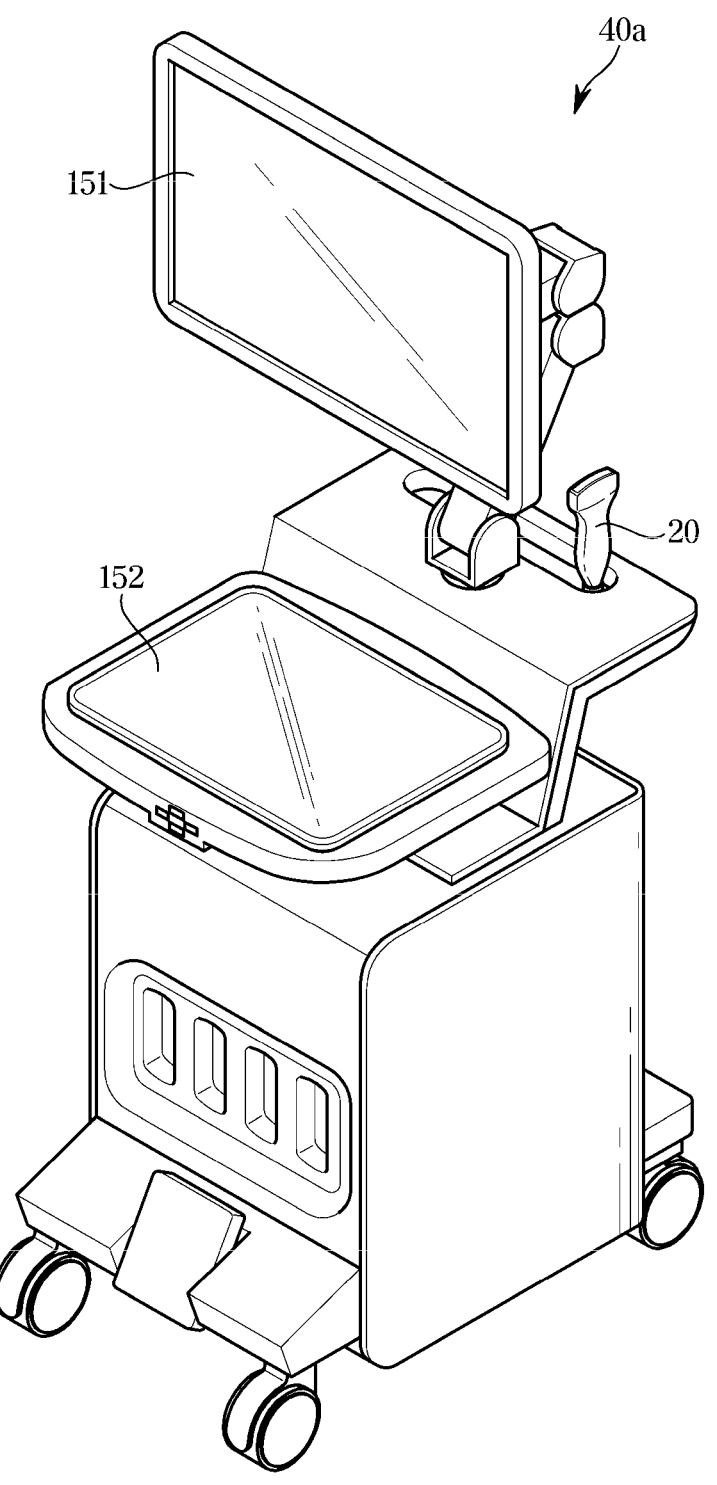
FIGS. 2A, 2B, 2C, and 2D are views illustrating the ultrasonic imaging device according to an embodiment.
Figure 2B:
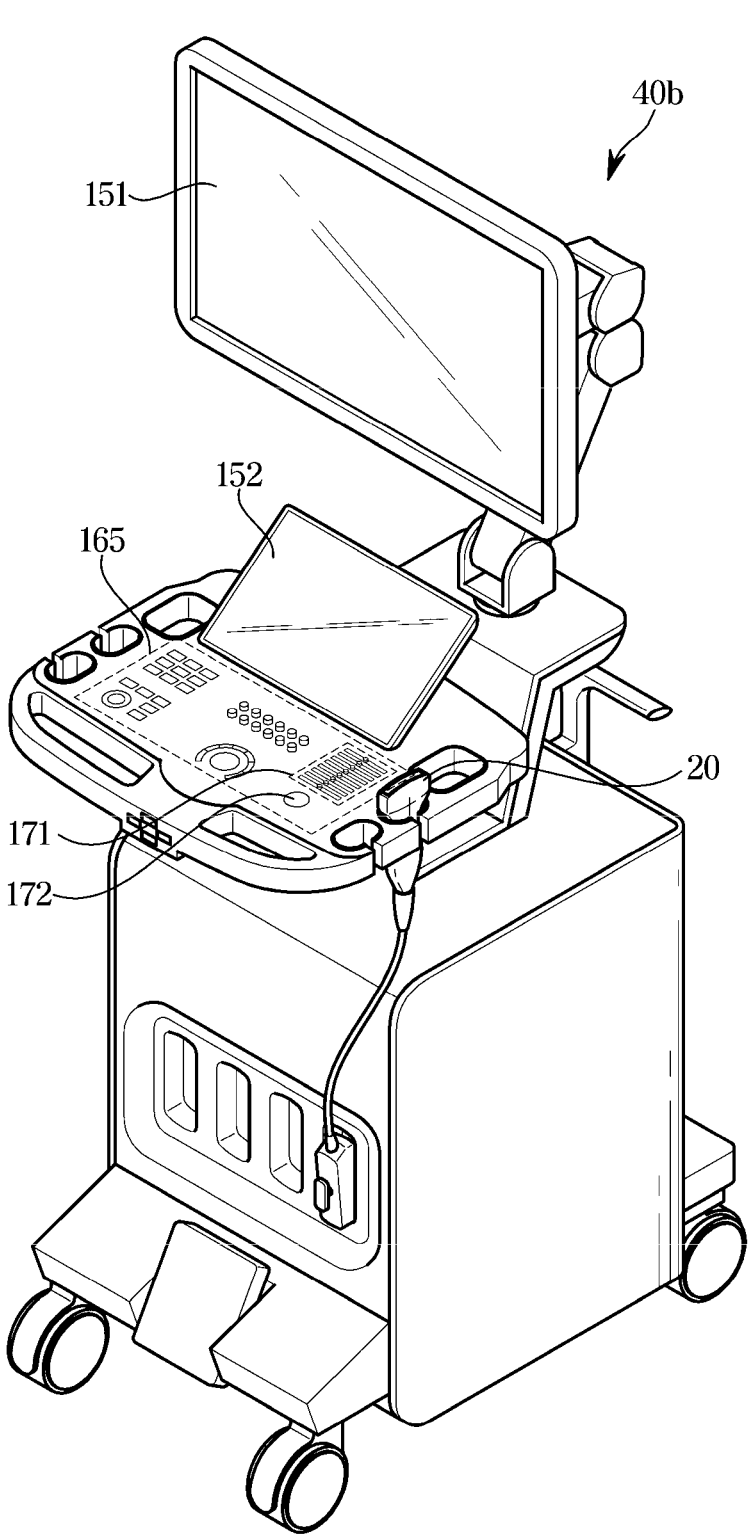
Figure 2C:
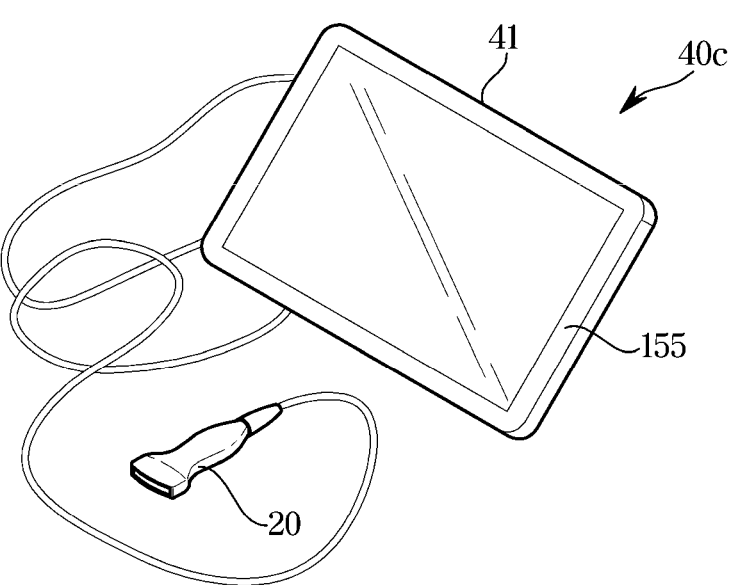
Figure 2D:
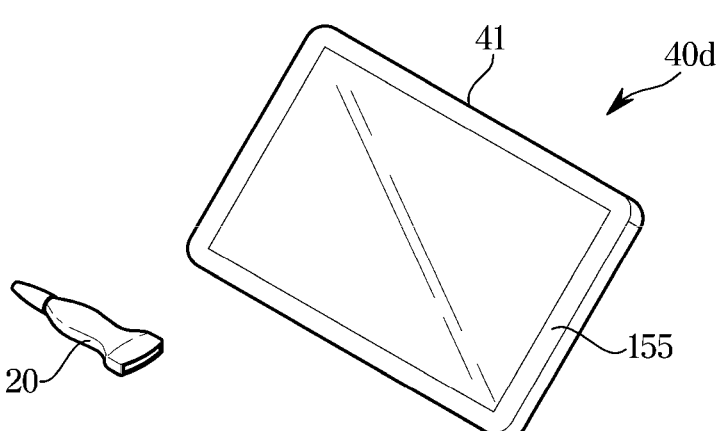

FIGS. 2A, 2A, 2C, and 2D are views illustrating ultrasonic imaging devices 40a, 40b, 40c, and 40d according to an embodiment.

Referring to FIGS. 2A and 2B, ultrasonic imaging devices 40a and 40b may include a main display 151 (150) and a sub display 152 (150). At least one of the main display 151 and the sub display 152 may be implemented as a touch screen. At least one of the main display 151 and the sub display 152 may display ultrasonic images or a variety of information processed by the ultrasonic imaging devices 40a and 40b. In addition, at least one of the main display 151 and the sub display 152 may be implemented as a touch screen and provide a GUI, so that data for controlling the ultrasonic imaging devices 40a and 40b may be inputted from the user. For example, the main display 151 may display an ultrasonic image, and the sub display 152 may display a control panel for controlling the display of the ultrasonic image in the form of a GUI. The sub display 152 may be provided with data for controlling the display of images through the control panel displayed in the form of a GUI. For example, a time gain compensation (TGC) button, a Freeze button, a trackball, a jog switch, a knob, and the like may be provided as a GUI on the sub display 152.

The ultrasonic imaging devices 40a and 40b may control the display of ultrasonic images displayed on the main display 151 using the inputted control data. The ultrasonic imaging devices 40a and 40b may also be connected to the probe 20 by wire or wirelessly to transmit and receive ultrasonic signals to and from the object 10.

Referring to FIG. 2B, the ultrasonic imaging device 40b may further include a control panel 165 in addition to the main display 151 and the sub display 152. The control panel 165 may include a button, a trackball, a jog switch, a knob, and the like, and may be provided with data for controlling the ultrasonic imaging device 40b from the user. For example, the control panel 165 may include a time gain compensation (TGC) button 171, a Freeze button 172, and the like. The TGC button 171 is a button for setting a TGC value for each depth of the ultrasonic images. When the input of the Freeze button 172 is sensed while scanning an ultrasonic image, the ultrasonic imaging device 40b may keep a state in which the frame image at that point in time is displayed.

A button, a trackball, a jog switch, a knob, and the like included in the control panel 165 may be provided as a GUI on the main display 151 or the sub display 152. The ultrasonic imaging devices 40a and 40b may be connected to the probe 20 to transmit and receive ultrasonic signals to and from the object 10.

Referring to FIGS. 2C and 2D, ultrasonic imaging devices 40c and 40d may also be implemented in a portable form. The portable ultrasonic imaging devices 40c and 40d may include, for example, a smart phone, laptop computer, PDA, tablet PC, etc., which include a probe and an application, but is not limited thereto.

The ultrasonic imaging device 40c may include a main body 41. Referring to FIG. 2C, the probe 20 may be connected to one side of the main body 41 by wire. To this end, the main body 41 may include a connection terminal to and from which a cable connected to the probe 20 may be attached and detached, and the probe 20 may include a connection terminal to and from which a cable connected to the main body 41 may be attached and detached.

Referring to FIG. 2D, the probe 20 may be wirelessly connected to the ultrasonic imaging device 40d. The main body 41 may include an input/output interface (e.g., a touch screen) 155 (150 and 170). Ultrasonic images, a variety of information processed by the ultrasonic imaging devices, GUIs, and the like may be displayed on the input/output interface 155.

An ultrasonic image may be displayed on the input/output interface 155. The ultrasonic imaging device 40d may correct the ultrasonic image displayed on the input/output interface 155 using AI. The ultrasonic imaging device 40d may provide an alarm for informing using various audio-visual tools, such as graphics, sound, and vibration, information about lesions among the ultrasonic images displayed on the input/output interface 155 using AI.

The ultrasonic imaging device 40d may output a control panel displayed in the form of a GUI through the input/output interface 155.

The ultrasonic imaging system 1 according to the disclosure may include the probe 20 configured to emit ultrasonic signals, and the ultrasonic imaging device 40 configured to wirelessly communicate with the probe 20.

The transducers 117 emitting ultrasonic signals are provided on opposite sides of the probe 20, respectively, and thus the probe 20 may include a total of the two transducers 117. This structure of the probe 20 is referred to as a so-called dual head structure.

The probe 20 may include transmitters 110 and 210 including the transmission module 113 and a receiver 600 including the reception module 115. The transmitters 110 and 210 may generate a transmission signal to be transmitted to the probe 20 for obtaining frames of ultrasound images. The frames of ultrasonic images may include frames of an A-mode (amplitude mode), B-mode (brightness mode), C-mode (color mode), D-mode (Doppler mode), E-mode (Elastography mode), M-mode (motion mode), Elastography, and the like.

The probe 20 may convert the transmission signal into an ultrasonic signal and emit the converted ultrasonic signal to a target region inside the object 10. The probe 20 may receive an echo signal, which is a reflected signal of an ultrasonic signal, and convert the echo signal to generate a reception signal. The receiver 600 may receive the converted reception signal from the probe 20.

To this end, the probe 20 may include the transducer 117 and a MUX circuit. The transducer 117 may convert an electrical signal into an ultrasonic signal or an ultrasonic signal into an electrical signal by vibrating.

The transducer 117 of the probe 20 may be implemented as a piezoelectric ultrasonic transducer using the piezoelectric effect. To this end, the transducer 117 may include a piezoelectric material or a piezoelectric thin film. When an alternating current is applied to a piezoelectric material or piezoelectric thin film from an internal storage device such as a battery or an external power supply, the piezoelectric material or piezoelectric thin film vibrates at a predetermined frequency, and an ultrasonic signal of a predetermined frequency is generated according to the vibration frequency.

When an echo signal of a predetermined frequency reaches the piezoelectric material or piezoelectric thin film, the piezoelectric material or piezoelectric thin film vibrates according to the frequency of the echo signal reached, and outputs an alternating current with a frequency corresponding to the vibration frequency.

In addition, the transducer 117 of the probe 20 may be implemented by another transducer such as a magnetostrictive ultrasonic transducer using the magnetostrictive effect of a magnetic material and a capacitive micromachined ultrasonic transducer (cMUT) transmitting and receiving ultrasonic waves using vibration of hundreds or thousands of micro-machined thin films.

As such, the transmitters 110 and 210 and the receiver 600 in the probe 20 may be key parts that directly affect performance. Therefore, it is very important to inspect whether the transmitters 110 and 210 and the receiver 600 are operating well as intended by the user.

The ultrasonic imaging system 1 according to the disclosure is configured to enable self-inspections of the transmitters 110 and 210 and the receiver 600 in the probe 20 having a dual head structure.

Figure 3A:
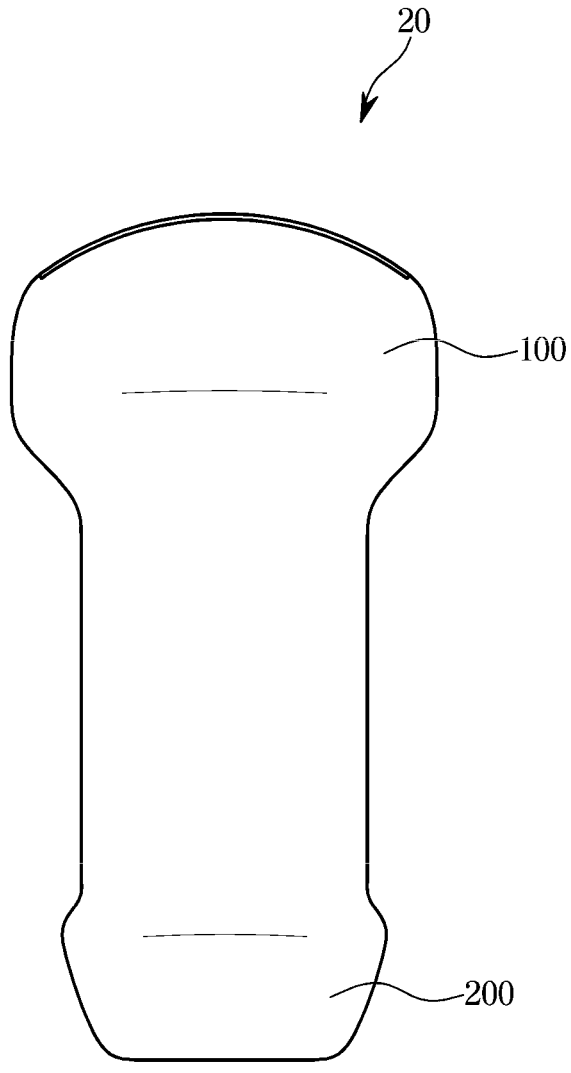
FIG. 3A is a view illustrating an outer appearance of a probe of the ultrasonic imaging system according to an embodiment.

FIG. 3A is a view illustrating an outer appearance of the probe 20 of the ultrasonic imaging system 1 according to an embodiment.

Figure 3B:
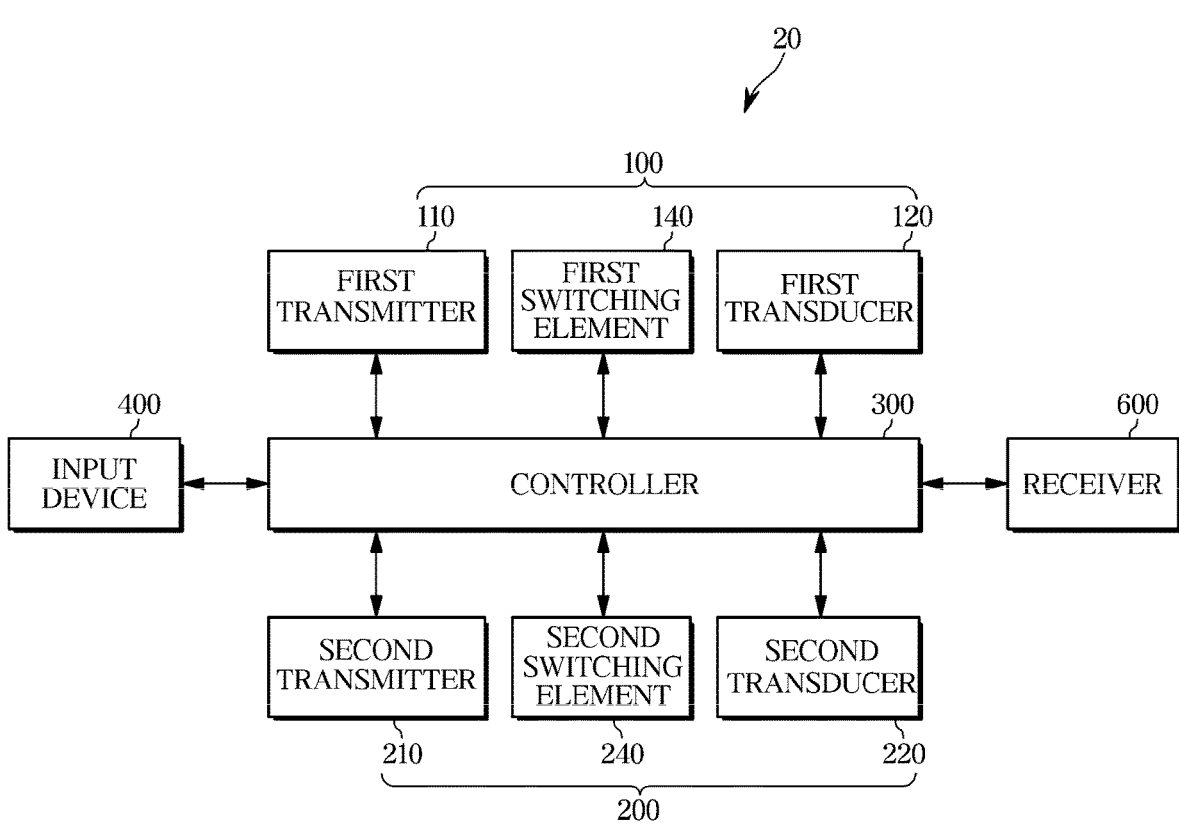
FIG. 3B is a control block diagram of the probe of the ultrasonic imaging system according to an embodiment.

FIG. 3B is a control block diagram of the probe 20 of the ultrasonic imaging system 1 according to an embodiment.

Figure 4:
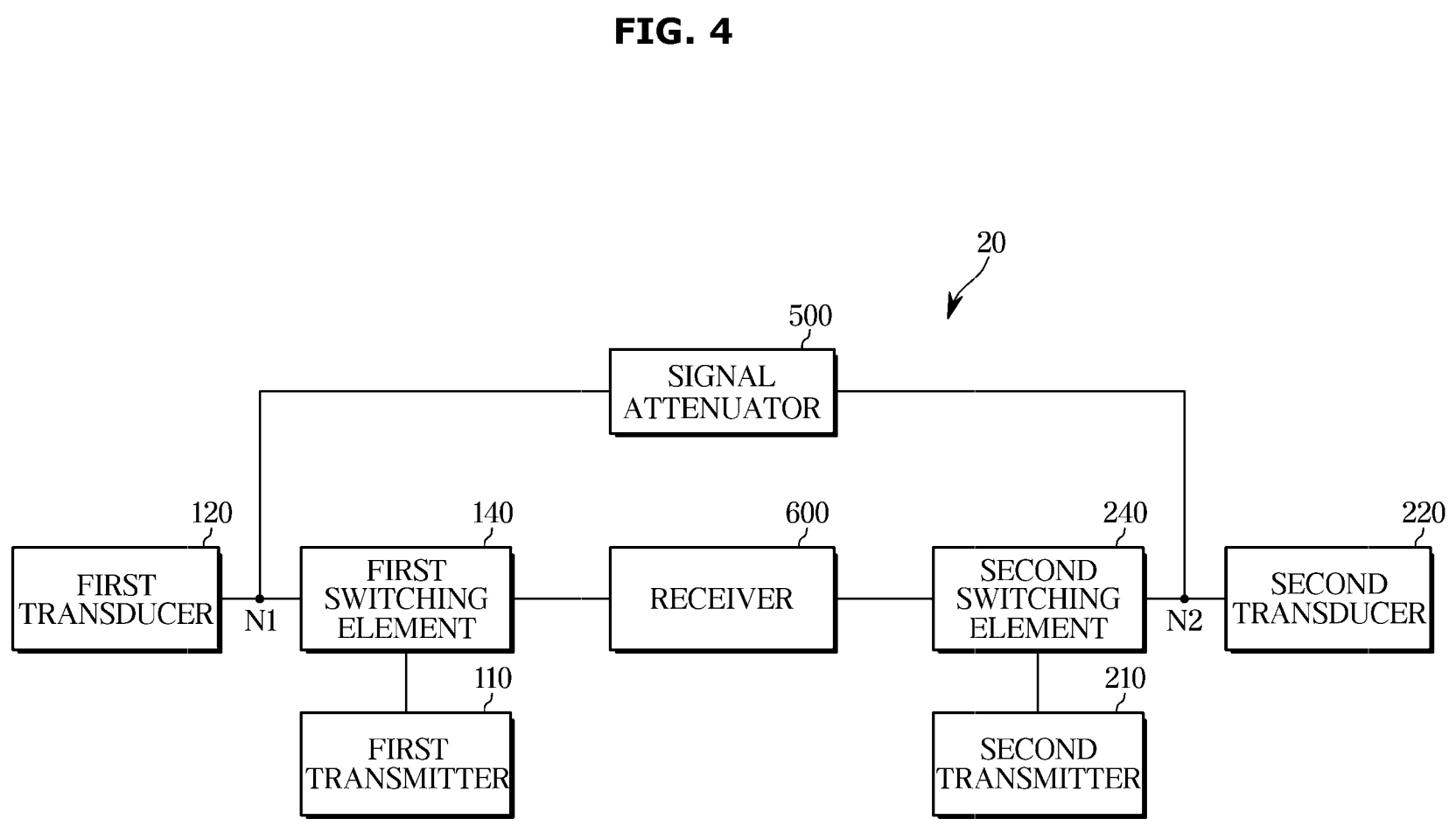

FIG. 4 is a block diagram illustrating briefly a circuit structure of the probe 20 of the ultrasonic imaging system 1 according to an embodiment.

Figure 5:
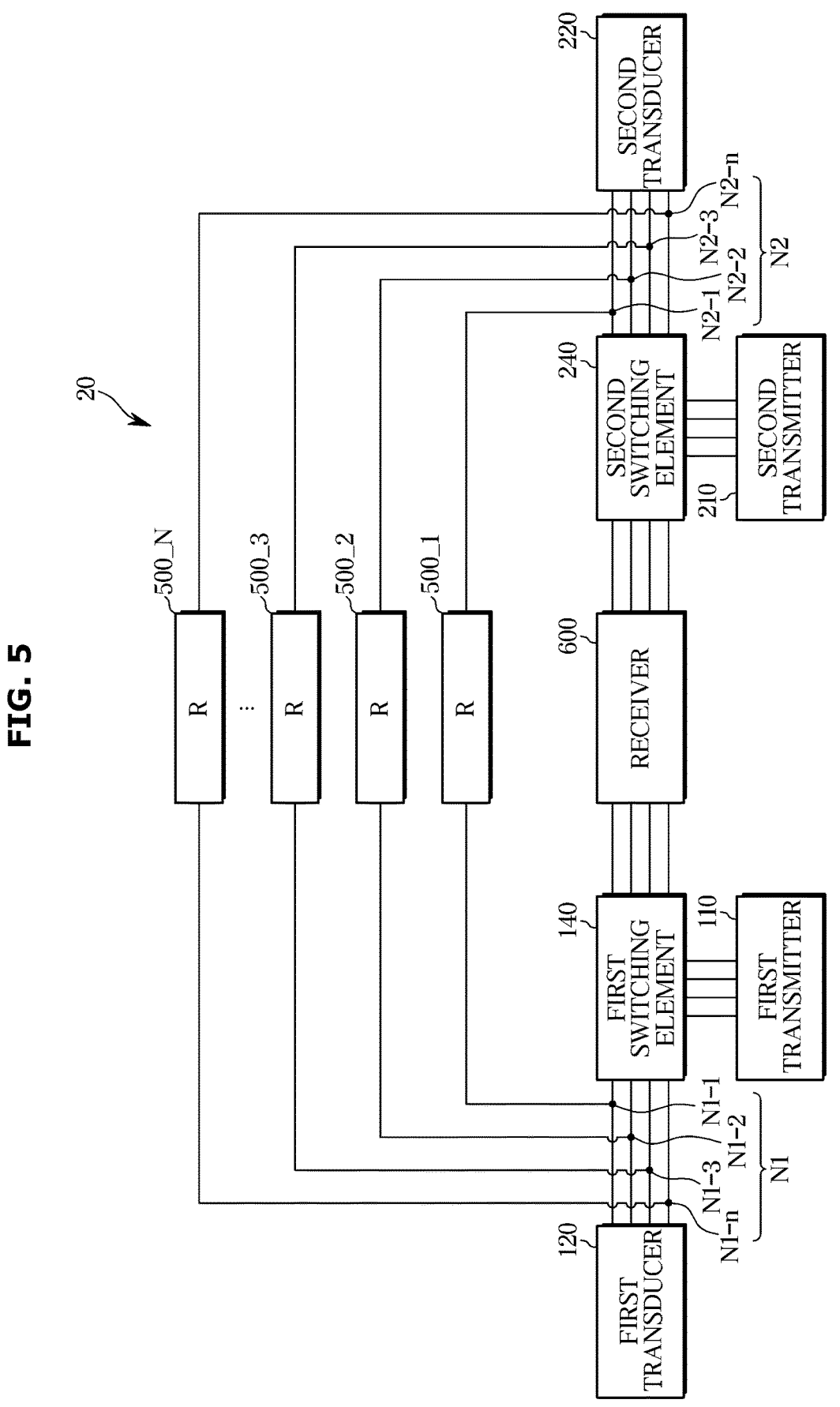
FIG. 5 is a block diagram illustrating in more detail the circuit structure of the probe of the ultrasonic imaging system according to an embodiment.

FIG. 5 is a block diagram illustrating in more detail the circuit structure of the probe 20 of the ultrasonic imaging system 1 according to an embodiment.

Referring to FIG. 3A, the probe 20 may be configured as a dual head structure. The probe 20 may include a first head part 100 provided on a first side and a second head part 200 provided on a second side.

Referring to FIGS. 3A, 3B, and 4, the probe 20 may include the first transmitter 110, a first transducer 120, a first switching element 140, the second transmitter 210, a second transducer 220, a second switching element 240, the receiver 600, a signal attenuator 500, an input device 400, and a controller 300 configured to control each of the above components.

The first switching element 140 may be connected to the first transducer 120, the first transmitter 110, and the receiver 600. The second switching element 240 may be connected to the second transducer 220, the second transmitter 210, and the receiver 600. That is, the receiver 600 may be connected to both the first switching element 140 and the second switching element 240.

The probe 20 of the ultrasonic imaging system 1 according to the disclosure may be configured as a dual head structure. Each of the head parts 100 and 200 may include a transducer.

The first head part 100 of the probe 20 may include the first transducer 120, the first transmitter 110, and the first switching element 140. The second head part 200 of the probe 20 may include the second transducer 220, the second transmitter 210, and the second switching element 240. The receiver 600 may be provided between the first head part 100 and the second head part 200.

However, the receiver 600 may be provided to have a different arrangement and structure depending on an intention of a designer. For example, the receiver 600 is included in the first head part 100, but may be provided to be connected to the second switching element 240, and is included in the second head part 200, but may be provided to be connected to the first switching element 140.

The first transducer 120 may include at least one first transducer element, and the first transducer element may mutually convert an electrical signal and an ultrasonic signal. The first transducer element may include a first transducer 120 array consisting of at least one row and at least one column.

The second transducer 220 may include at least one second transducer element, and the second transducer element may mutually convert an electrical signal and an ultrasonic signal. The second transducer element may include the second transducer 220 array consisting of at least one row and at least one column.

The first transmitter 110 may include one or more first transmission elements, the second transmitter 210 may include one or more second transmission elements, and the receiver 600 may include one or more reception elements.

Each of the one or more first transmission elements may be connected to each of the one or more first transducer elements. Each of the one or more reception elements may be connected to each of the one or more first transducer elements.

Each of the one or more second transmission elements may be connected to each of the one or more second transducer elements. Each of the one or more reception elements may be connected to each of the one or more second transducer elements.

The first transmitter 110 may generate and output a first transmission signal. The generated first transmission signal may be transmitted to the first transducer 120 through the first switching element 140. Each of the one or more first transmission elements included in the first transmitter 110 may transmit the first transmission signal to each of the one or more first transducer elements through the first switching element 140.

The first transmission signal may be an electrical signal. The first transmitter 110 may output the first transmission signal depending on a control signal from the controller 300. The first transmitter 110 may output the first transmission signal with a delay by a set time based on a synchronization signal having a repetition frequency. Through this, the first transmission signal may be a pulse having a repetition frequency. The first transmission signal may generally use a high voltage signal.

The first transducer 120 may convert the transmitted first transmission signal into a first ultrasonic signal. The first transducer 120 may emit the converted first ultrasonic signal to the object 10. Specifically, the first transducer 120 may emit the first ultrasonic signal to the target region inside the object 10.

The first transducer 120 may receive a first echo signal in which the emitted first ultrasonic signal is reflected from the target region inside the object 10. The first transducer 120 may generate and output a first reception signal based on the received first echo signal. The generated first reception signal may be transmitted to the receiver 600 through the first switching element 140.

The one or more first transducer elements included in the first transducer 120 may be arranged on one surface of a first housing of the first transducer 120. Specifically, the one or more first transducer elements may be arranged in a direction parallel to a first opening so that the first ultrasonic signal and the first echo signal may be transmitted and received through the first opening provided on the one surface of the first housing.

The receiver 600 may receive the first reception signal outputted from the first transducer 120 through the first switching element 140. The first reception signal may correspond to a low voltage signal compared to the first transmission signal, which is a high voltage signal. Therefore, in general, the receiver 600 may use a range corresponding to a voltage of the first reception signal generated from the first transducer 120 as an input range.

Each of the one or more shared reception elements may receive the first reception signal from each of the one or more first transducer elements through the first switching element 140.

The first switching element 140 may transmit the first transmission signal outputted from the first transmitter 110 to the first transducer 120. The first reception signal received from the first transducer 120 may be transmitted to the receiver 600.

In a state in which the first switching element 140 is turned off, the first transmission signal generated from the first transmitter 110 may be transmitted to the first transducer 120 through the first switching element 140. In a state in which the first switching element 140 is turned on, the first reception signal generated from the first transducer 120 may be transmitted to the receiver 600 through the first switching element 140.

The second transmitter 210 may generate and output a second transmission signal. The generated second transmission signal may be transmitted to the second transducer 220 through the second switching element 240. Each of the one or more second transmission elements included in the second transmitter 210 may transmit the second transmission signal to each of the one or more second transducer elements through the second switching element 240.

The second transmission signal may be an electrical signal. The second transmitter 210 may output the second transmission signal depending on a control signal from the controller 300. The second transmitter 210 may output the second transmission signal with a delay by a set time based on a synchronization signal having a repetition frequency. Through this, the second transmission signal may be a pulse having a repetition frequency. The second transmission signal may generally use a high voltage signal.

The second transducer 220 may convert the transmitted second transmission signal into a second ultrasonic signal. The second transducer 220 may emit the converted second ultrasonic signal to the object 10. Specifically, the second transducer 220 may emit the second ultrasonic signal to the target region inside the object 10.

The second transducer 220 may receive a second echo signal in which the emitted second ultrasonic signal is reflected from the target region inside the object 10. The second transducer 220 may generate and output a second reception signal based on the received second echo signal. The generated second reception signal may be transmitted to the receiver 600 through the second switching element 240.

The one or more second transducer elements included in the second transducer 220 may be arranged on one surface of a second housing of the second transducer 220. Specifically, the one or more second transducer elements may be arranged in a direction parallel to a second opening so that the second ultrasonic signal and the second echo signal may be transmitted and received through the second opening provided on the one surface of the second housing.

The receiver 600 may receive the second reception signal outputted from the second transducer 220 through the second switching element 240. The second reception signal may correspond to a low voltage signal compared to the second transmission signal, which is a high voltage signal. Therefore, in general, the receiver 600 may use a range corresponding to a voltage of the second reception signal generated from the second transducer 220 as an input range.

Each of the one or more reception elements may receive the second reception signal from each of the one or more second transducer elements through the second switching element 240.

The second switching element 240 may transmit the second transmission signal outputted from the second transmitter 210 to the second transducer 220. The second reception signal received from the second transducer 220 may be transmitted to the receiver 600.

In a state in which the second switching element 240 is turned off, the second transmission signal generated from the second transmitter 210 may be transmitted to the second transducer 220 through the second switching element 240. In a state in which the second switching element 240 is turned on, the second reception signal generated from the second transducer 220 may be transmitted to the receiver 600 through the second switching element 240.

Referring to FIGS. 4 and 5, the probe 20 of the ultrasonic imaging system 1 according to the disclosure may further include a first node N1 provided between the first transducer 120 and the first switching element 140, and a second node N2 provided between the second transducer 220 and the second switching element 240.

The signal attenuator 500 may be connected between the first node N1 and the second node N2. The signal attenuator 500 may include at least one resistor element R. Accordingly, when a plurality of the resistance elements R is provided, a plurality of the first nodes N1 and a plurality of the second nodes N2 may be provided connected to a plurality of resistance elements (500_1, 500_2, 500_3, . . . , 500_N), respectively.

However, as illustrated in FIG. 5, the plurality of first nodes N1 connected to the plurality of first transducer elements and the plurality of second nodes N2 connected to the plurality of second transducer elements do not have to be connected in order.

For example, it may be assumed that the plurality of first nodes N1 includes N1-1, N1-2, and N1-3, the plurality of second nodes N2 includes N2-1, N2-2, and N2-3, and there is the plurality of resistance elements (500_1, 500_2, 500_3, . . . , 500_N) R_1, R_2, and R_3. Herein, as illustrated in FIG. 5, R_1 may be connected between N1-1 and N2-1, R_2 may be connected between N1-2 and N2-2, and R_3 may be connected between N1-3 and N2-3. However, R_1 may be connected between N1-2 and N2-1, R_2 may be connected between N1-1 and N2-2, and R_3 may be connected between N1-3 and N2-2. In addition, because as long as it is a connectable combination, the plurality of first nodes N1, the plurality of second nodes N2, and the plurality of resistance elements 500_1, 500_2, 500_3, . . . , 500_N may be provided in any way, the disclosure is not limited to the example of FIG. 5.

The signal attenuator 500 may attenuate an intensity of the first transmission signal outputted from the first transmitter 110. Specifically, in the state in which the first switching element 140 is turned off, the first transmission signal may be attenuated through the signal attenuator 500 and transmitted to the second switching element 240.

The signal attenuator 500 may also attenuate an intensity of the second transmission signal outputted from the second transmitter 210. Specifically, in the state in which the second switching element 240 is turned off, the second transmission signal may be attenuated through the signal attenuator 500 and transmitted to the first switching element 140.

When the signal attenuator 500 is disposed in the above structure, the signal attenuator 500 may be free from a parasitic capacitance compared to a conventional structure of being connected in parallel with the first switching element 140 or the second switching element 240, so that more accurate inspection is possible.

In addition, the signal attenuator 500 is not disposed in each of the first head part 100 and the second head part 200, but the single signal attenuator 500 connecting both the head parts is disposed, so that the number of circuit elements may be reduced significantly.

The input device 400 may receive a signal for at least one of a first inspection mode and a second inspection mode. When the controller 300 receives signals for both the first inspection mode and the second inspection mode through the input device 400, the controller 300 may sequentially perform the first inspection mode and the second inspection mode.

A subject of input may be the user, and the user may set such that a signal for at least one of the first inspection mode and the second inspection mode is automatically inputted through the controller 300 when a specific condition is met. For example, the user may set such that a signal for the first inspection mode or the second inspection mode is inputted based on a predetermined period.

The first inspection mode may be to inspect first operating states of the first transmitter 110 and the receiver 600, and the second inspection mode may be to inspect second operating states of the second transmitter 210 and the receiver 600. The first operating states may include whether the first transmitter 110 and the receiver 600 are operating normally, performance level, noise, etc. The second operating states may include whether the second transmitter 210 and the receiver 600 are operating normally, performance level noise, etc.

That is, the input device 400 may obtain a command for performing at least one of the first inspection mode for inspecting the first operating states and the second inspection mode for inspecting the second operating states.

The controller 300 may control the operations of the internal components of the probe 20. The controller 300 may include at least one memory storing a program for performing an operation of the probe 20 of the ultrasonic imaging system 1 and at least one processor executing the stored program.

The memory and the processor may be implemented as separate chips. The processor may include one or more processor chips or may include one or more processing cores. The memory may include one or more memory chips or may include one or more memory blocks. The memory and the processor may also be implemented as a single chip.

Specific control operations of the controller 300 will be described later.

Figure 6:
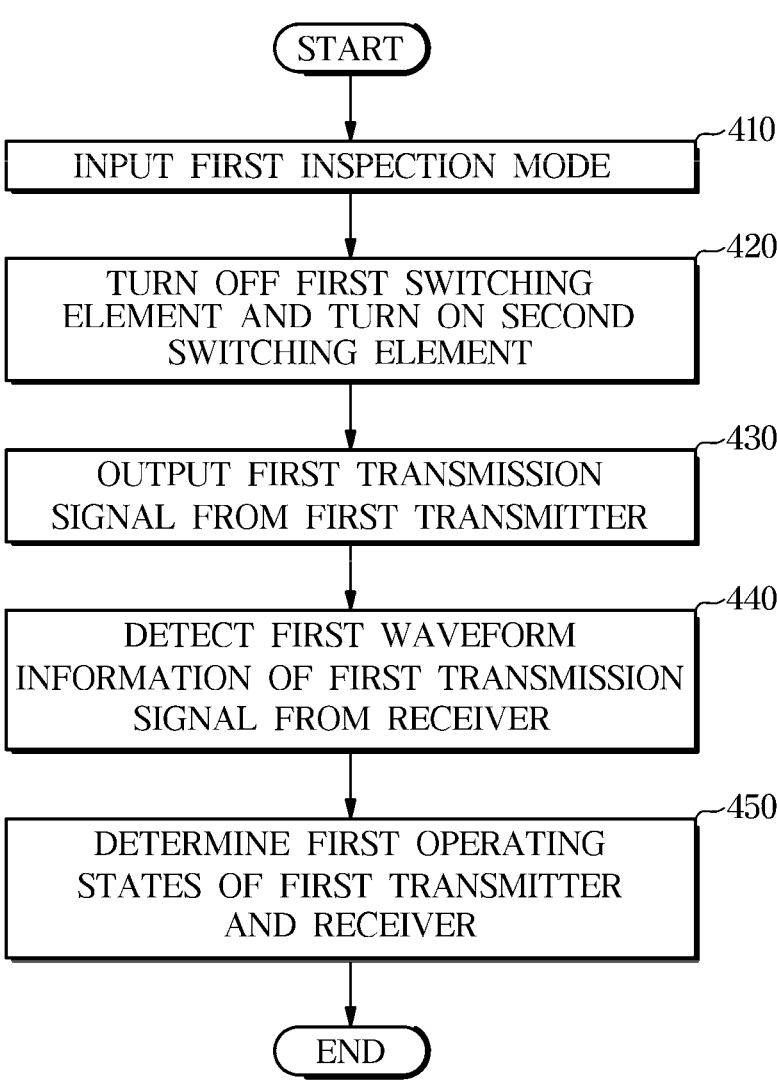
FIG. 6 is a flowchart illustrating a method of controlling the probe of the ultrasonic imaging system according to an embodiment.

FIG. 6 is a flowchart illustrating a method of controlling the probe 20 of the ultrasonic imaging system 1 according to an embodiment.

Referring to FIG. 6, the controller 300 may control the input device 400 to obtain the command for performing the first inspection mode or the second inspection mode. Accordingly, a signal for the first inspection mode may be inputted to the input device 400 (410).

The controller 300 may turn off the first switching element 140 and turn on the second switching element 240 based on the command for performing the first inspection mode obtained through the input device 400 (420). Herein, turning off the first switching element 140 refers to operating such that the first transmitter 110 and the signal attenuator 500 are connected. Also, turning on the second switching element 240 refers to operating such that the receiver 600 and the signal attenuator 500 are connected.

The controller 300 may also control the first transmitter 110 to generate and output the first transmission signal from the first transmitter 110 based on the command for performing the first inspection mode obtained through the input device 400 (430).

In the state in which the first switching element 140 is turned off, the first transmission signal outputted from the first transmitter 110 may be transmitted to the signal attenuator 500, and the intensity of the first transmission signal may be attenuated through the signal attenuator 500. In the state in which the second switching element 240 is turned on, the first transmission signal transmitted through the signal attenuator 500 may be transmitted to the receiver 600. The receiver 600 may receive the attenuated first transmission signal.

The controller 300 may control the receiver 600 to detect first waveform information of the received first transmission signal (440).

The controller 300 may determine whether the first operating states of the first transmitter 110 and the receiver 600 is normal based on the first waveform information detected from the receiver 600 (450). Specifically, the controller 300 may inspect the first operating state based on the first waveform information of the first transmission signal detected from the receiver 600 by changing at least one of a frequency and the intensity of the first transmission signal generated from the first transmitter 110. The controller 300 may also inspect the first operating state based on the first waveform information of the first transmission signal detected from the receiver 600 by changing at least one of a gain, bandwidth, and impedance of the receiver 600.

As such, the controller 300 may determine whether the first transmitter 110 and the receiver 600 are abnormal based on the signal for the first inspection mode inputted through the input device 400.

Figure 7:
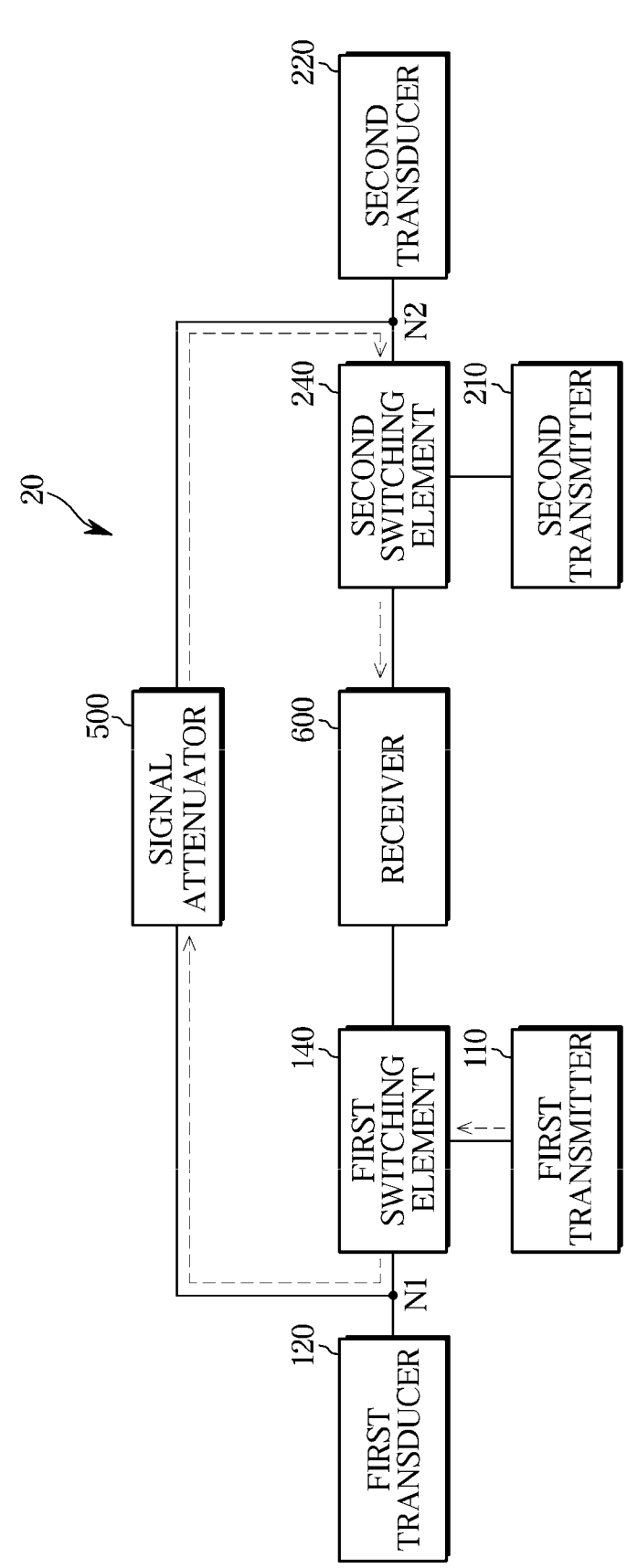
FIG. 7 is a diagram illustrating a control operation of a controller on a circuit diagram of the probe of the ultrasonic imaging system according to an embodiment.

FIG. 7 is a diagram illustrating a control operation of the controller 300 on a circuit diagram of the probe 20 of the ultrasonic imaging system 1 according to an embodiment.

Referring to FIG. 7, the controller 300 may perform a series of control operations for inspecting the first operating states of the first transmitter 110 and the receiver 600.

The controller 300 may control the first transmitter 110 to generate the first transmission signal. The first transmission signal generated from the first transmitter 110 may be transmitted to the first switching element 140.

The controller 300 may control the first switching element 140 to be turned off based on receiving the first transmission signal. That is, the controller 300 may control the first switching element 140 such that the first transmitter 110 and the signal attenuator 500 are connected. Accordingly, the first transmission signal may be transmitted to the signal attenuator 500.

The signal attenuator 500 may attenuate the intensity of the first transmission signal, and the attenuated first transmission signal may be transmitted to the second switching element 240.

The controller 300 may control the second switching element 240 to be turned on based on receiving the attenuated first transmission signal. That is, the controller 300 may control the second switching element 240 such that the receiver 600 and the signal attenuator 500 are connected. Accordingly, the attenuated first transmission signal may be transmitted to the receiver 600.

Figure 8:
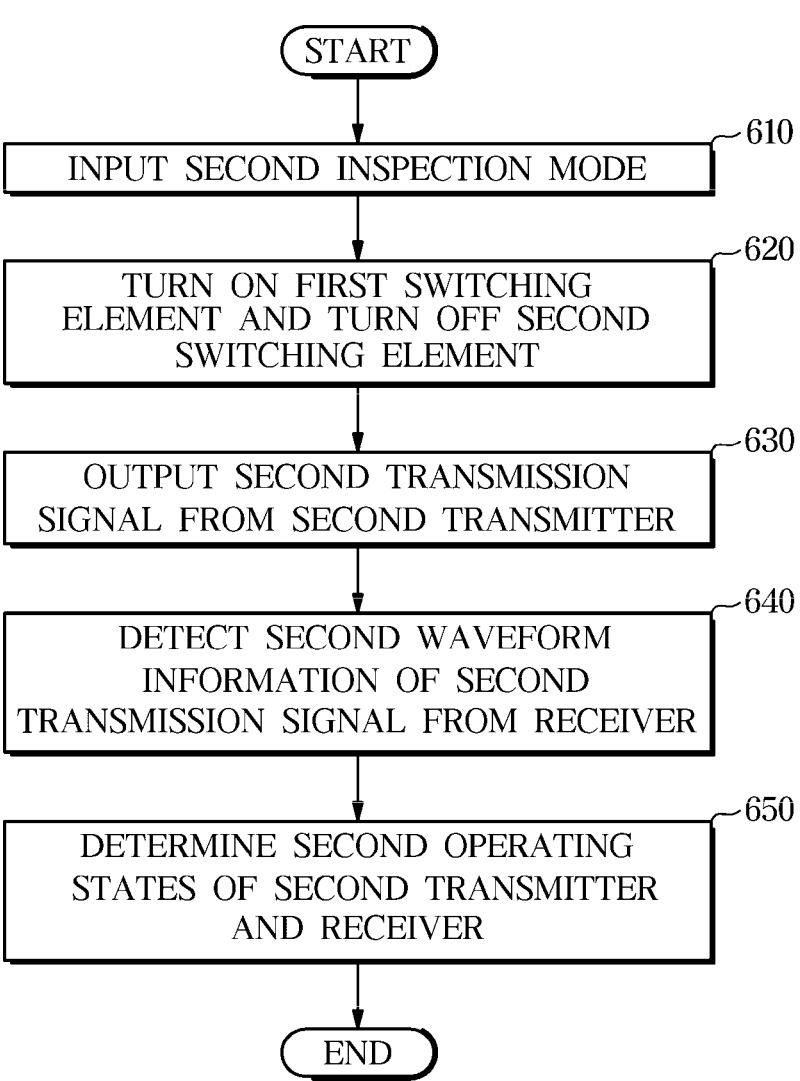
FIG. 8 is a flowchart illustrating a method of controlling the probe of the ultrasonic imaging system according to another embodiment.

FIG. 8 is a flowchart illustrating a method of controlling the probe 20 of the ultrasonic imaging system 1 according to another embodiment.

Referring to FIG. 8, the controller 300 may control the input device 400 to obtain the command for performing the first inspection mode or the second inspection mode. Accordingly, a signal for the second inspection mode may be inputted to the input device 400 (610).

The controller 300 may turn on the first switching element 140 and turn off the second switching element 240 based on the command for performing the second inspection mode obtained through the input device 400 (620). Herein, turning on the first switching element 140 refers to operating such that the first transmitter 110 and the signal attenuator 500 are connected. Also, turning off the second switching element 240 refers to operating such that the second transmitter 210 and the signal attenuator 500 are connected.

The controller 300 may also control the second transmitter 210 to generate and output the second transmission signal from the second transmitter 210 based on the command for performing the second inspection mode obtained through the input device 400 (630).

In the state in which the second switching element 240 is turned off, the second transmission signal outputted from the second transmitter 210 may be transmitted to the signal attenuator 500, and the intensity of the second transmission signal may be attenuated through the signal attenuator 500. In the state in which the first switching element 140 is turned on, the second transmission signal transmitted through the signal attenuator 500 may be transmitted to the receiver 600. The receiver 600 may receive the attenuated second transmission signal.

The controller 300 may control the receiver 600 to detect second waveform information of the received second transmission signal (640). Specifically, the controller 300 may inspect the second operating state based on the second waveform information of the second transmission signal detected from the receiver 600 by changing at least one of a frequency and the intensity of the second transmission signal generated from the second transmitter 210. The controller 300 may also inspect the second operating state based on the second waveform information of the second transmission signal detected from the receiver 600 by changing at least one of the gain, bandwidth, and impedance of the receiver 600.

The controller 300 may determine whether the second operating states of the second transmitter 210 and the receiver 600 are normal based on the second waveform information detected from the receiver 600 (650).

As such, the controller 300 may determine whether the second transmitter 210 and the receiver 600 are abnormal based on the signal for the second inspection mode inputted through the input device 400.

FIG. 9 is a diagram illustrating a control operation of the controller 300 on the circuit diagram of the probe 20 of the ultrasonic imaging system 1 according to another embodiment.

Referring to FIG. 9, the controller 300 may perform a series of control operations for inspecting the second operating states of the second transmitter 210 and the receiver 600.

The controller 300 may control the second transmitter 210 to generate the second transmission signal. The second transmission signal generated from the second transmitter 210 may be transmitted to the second switching element 240.

The controller 300 may control the second switching element 240 to be turned off based on receiving the second transmission signal. That is, the controller 300 may control the second switching element 240 such that the second transmitter 210 and the signal attenuator 500 are connected. Accordingly, the second transmission signal may be transmitted to the signal attenuator 500.

The signal attenuator 500 may attenuate the intensity of the second transmission signal, and the attenuated second transmission signal may be transmitted to the first switching element 140.

The controller 300 may control the first switching element 140 to be turned on based on receiving the attenuated second transmission signal. That is, the controller 300 may control the first switching element 140 such that the receiver 600 and the signal attenuator 500 are connected. Accordingly, the attenuated second transmission signal may be transmitted to the receiver 600.

Therefore, the self-inspection of the receiver 600 is possible without an additional controller according to the disclosure.

Figure 10:
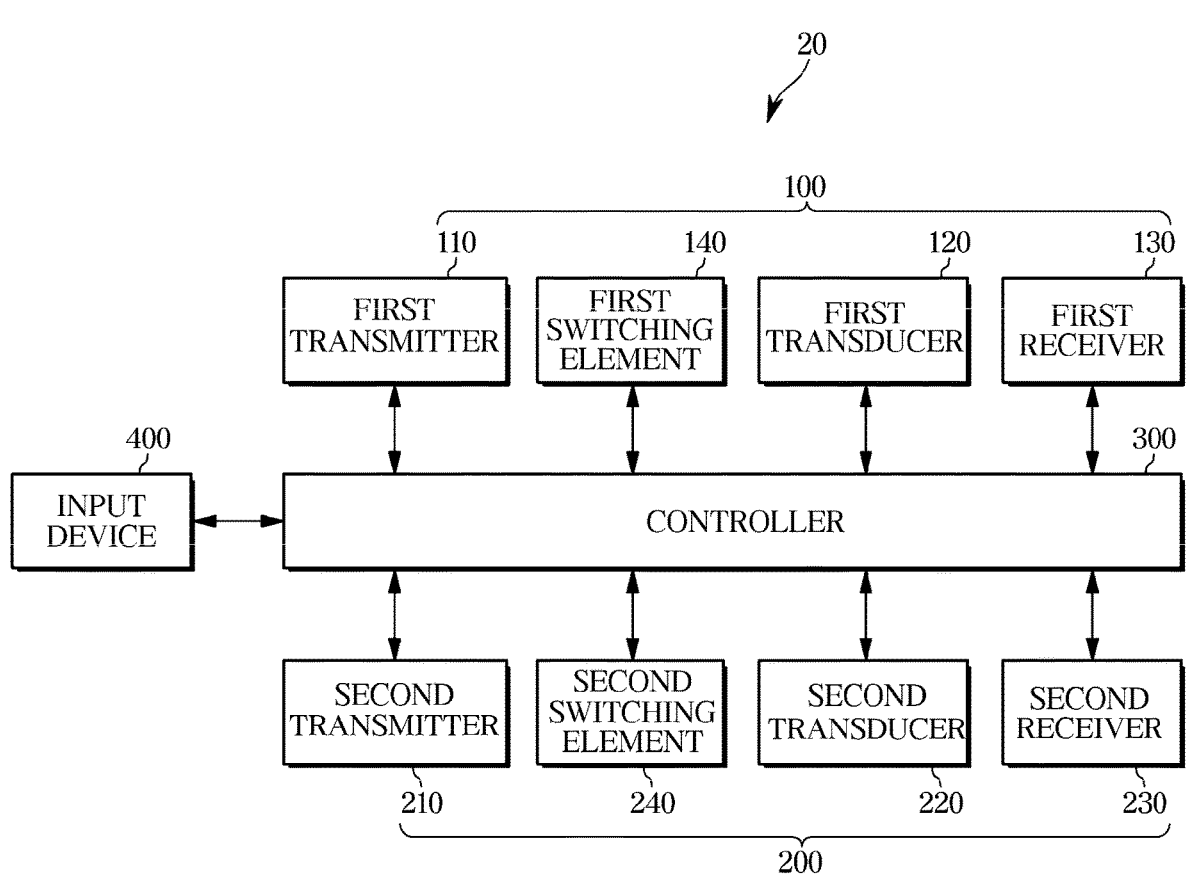
FIG. 10 is a control block diagram of the probe of the ultrasonic imaging system according to another embodiment.

FIG. 10 is a control block diagram of the probe 20 of the ultrasonic imaging system 1 according to another embodiment.

Figure 11:
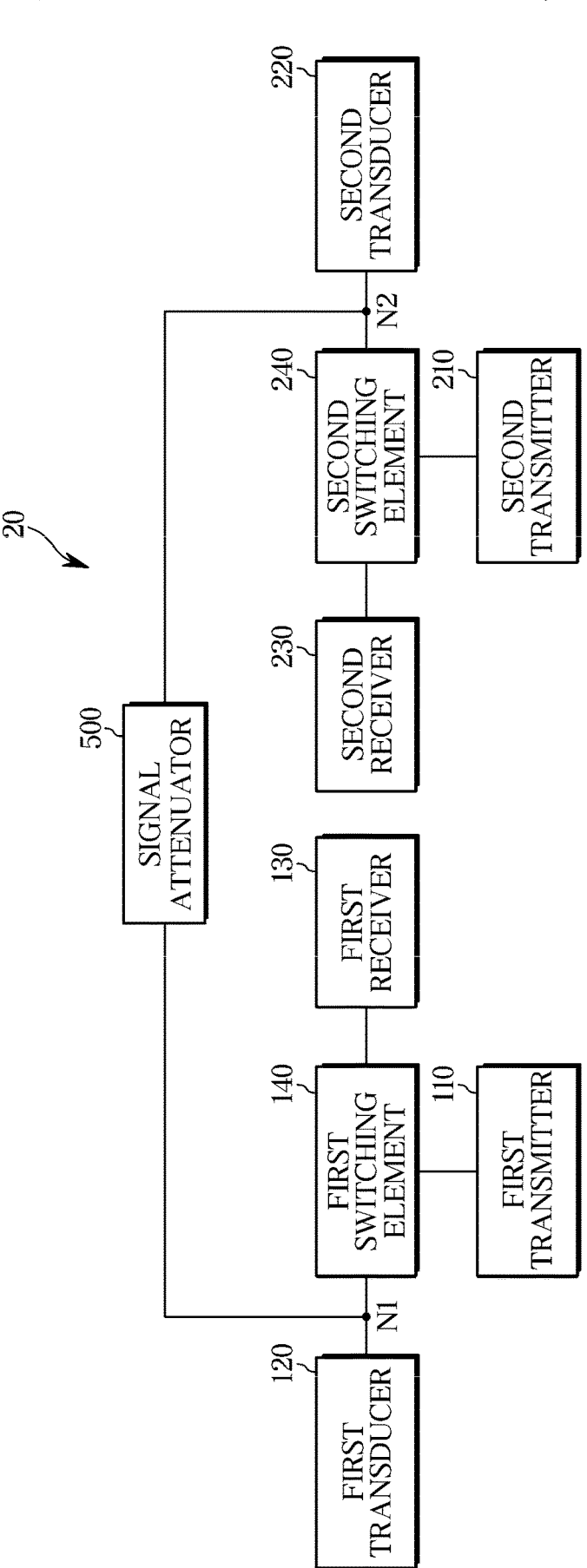
FIG. 11 is a block diagram illustrating briefly a circuit structure of the probe of the ultrasonic imaging system according to another embodiment.

FIG. 11 is a block diagram illustrating briefly a circuit structure of the probe 20 of the ultrasonic imaging system 1 according to another embodiment.

Figure 12:
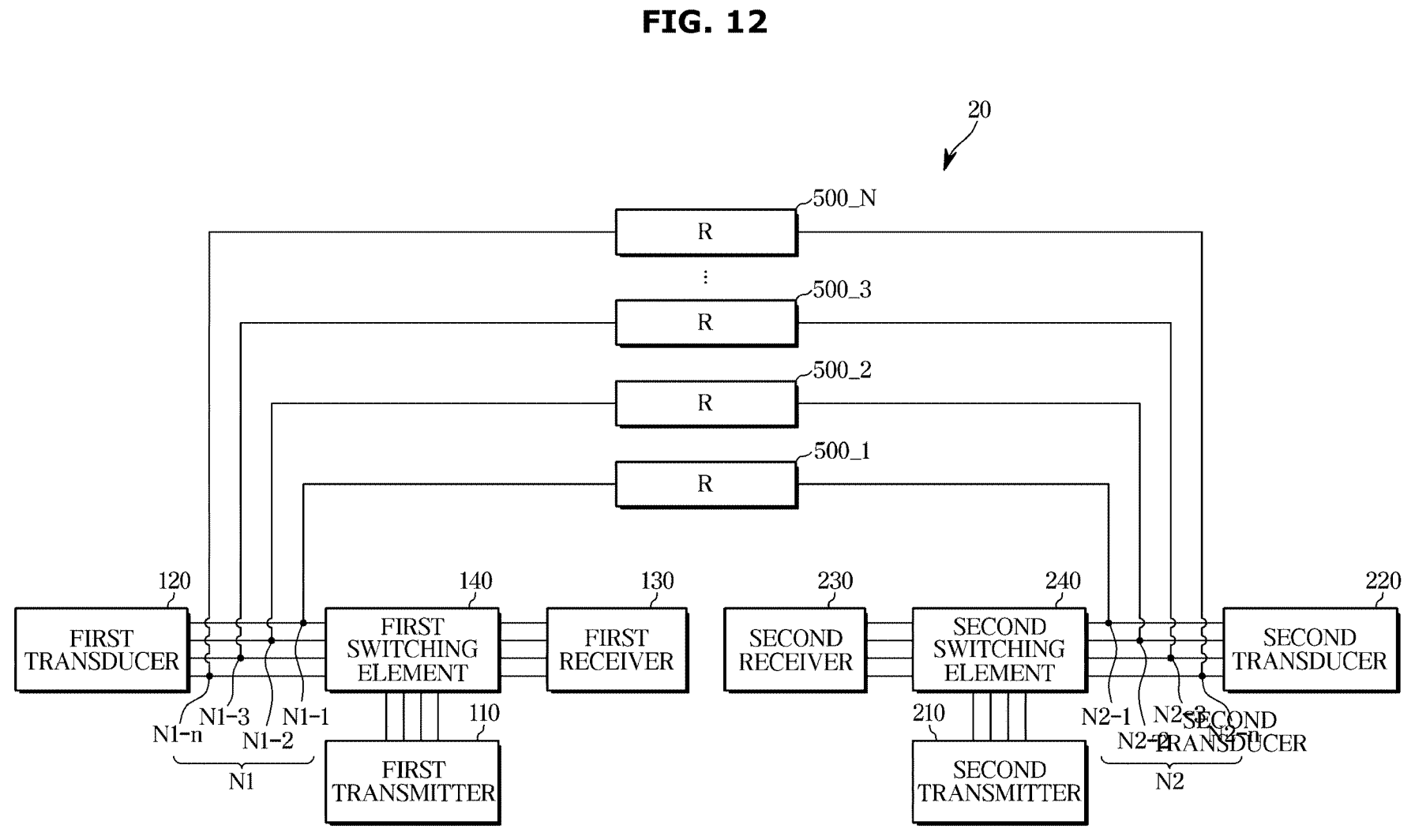

FIG. 12 is a block diagram illustrating in more detail the circuit structure of the probe 20 of the ultrasonic imaging system 1 according to another embodiment.

Figure 13:
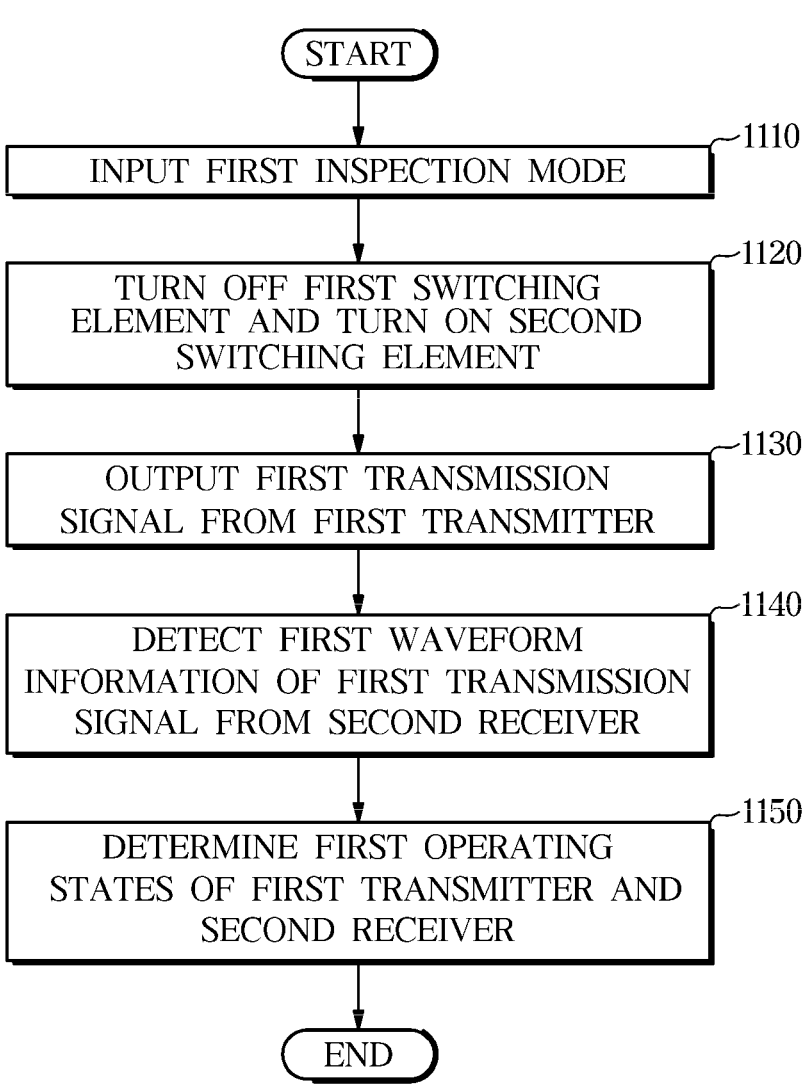
FIG. 13 is a flowchart illustrating a method of controlling the probe of the ultrasonic imaging system according to another embodiment.

Referring to FIGS. 12 and 13, the probe 20 of the ultrasonic imaging system 1 may include the first transmitter 110, the first transducer 120, a first receiver 130, the first switching element 140, the second transmitter 210, the second transducer 220, a second receiver 230, the second switching element 240, the signal attenuator 500, the input device 400, and the controller 300 configured to control each of the above components.

The first switching element 140 may be connected to the first transducer 120, the first transmitter 110, and the first receiver 130. The second switching element 240 may be connected to the second transducer 220, the second transmitter 210, and the second receiver 230.

The probe 20 of the ultrasonic imaging system 1 according to the disclosure may be configured as a dual head structure. Each of the head parts 100 and 200 may include a transducer.

The first head part 100 provided on the first side of the probe 20 may include the first transducer 120, the first transmitter 110, the first receiver 130, and the first switching element 140. The second head part 200 provided on the second side of the probe 20 may include the second transducer 220, the second transmitter 210, the second receiver 230, and the second switching element 240.

The first transducer 120 may include the at least one first transducer element, and the first transducer element may mutually convert an electrical signal and an ultrasonic signal.

The second transducer 220 may include the at least one second transducer element, and the second transducer element may mutually convert an electrical signal and an ultrasonic signal.

The first transmitter 110 may include the one or more first transmission element, the second transmitter 210 may include the one or more second transmission elements, the first receiver 130 may include one or more first reception elements, and the second receiver 230 may include one or more second reception elements.

Each of the one or more first transmission elements may be connected to each of the one or more first transducer elements. Each of the one or more first reception elements may be connected to each of the one or more first transducer elements.

Each of the one or more second transmission elements may be connected to each of the one or more second transducer elements. Each of the one or more second reception elements may be connected to each of the one or more second transducer elements.

The first transmitter 110 may generate and output the first transmission signal. The generated first transmission signal may be transmitted to the first transducer 120 through the first switching element 140. Each of the one or more first transmission elements included in the first transmitter 110 may transmit the first transmission signal to each of the one or more first transducer elements through the first switching element 140.

The first transmission signal may be an electrical signal. The first transmitter 110 may output the first transmission signal depending on a control signal from the controller 300. The first transmitter 110 may output the first transmission signal with the delay by the set time based on the synchronization signal having the repetition frequency. Through this, the first transmission signal may be a pulse having the repetition frequency. The first transmission signal may generally use a high voltage signal.

The first transducer 120 may convert the transmitted first transmission signal into the first ultrasonic signal. The first transducer 120 may emit the converted first ultrasonic signal to the object 10. Specifically, the first transducer 120 may emit the first ultrasonic signal to the target region inside the object 10.

The first transducer 120 may receive the first echo signal in which the emitted first ultrasonic signal is reflected from the target region inside the object 10. The first transducer 120 may generate and output the first reception signal based on the received first echo signal. The generated first reception signal may be transmitted to the first receiver 130 through the first switching element 140.

The one or more first transducer elements included in the first transducer 120 may be arranged on one surface of the first housing of the first transducer 120. Specifically, the one or more first transducer elements may be arranged in the direction parallel to the first opening so that the first ultrasonic signal and the first echo signal may be transmitted and received through the first opening provided on the one surface of the first housing.

The first receiver 130 may receive the first reception signal outputted from the first transducer 120 through the first switching element 140. The first reception signal may correspond to a low voltage signal compared to the first transmission signal, which is a high voltage signal. Therefore, in general, the first receiver 130 may use a range corresponding to a voltage of the first reception signal generated from the first transducer 120 as an input range.

Each of the one or more first reception elements may receive the first reception signal from each of the one or more first transducer elements through the first switching element 140.

The first switching element 140 may transmit the first transmission signal outputted from the first transmitter 110 to the first transducer 120. The first reception signal received from the first transducer 120 may be transmitted to the first receiver 130.

In the state in which the first switching element 140 is turned off, the first transmission signal generated from the first transmitter 110 may be transmitted to the first transducer 120 through the first switching element 140. In a state in which the first switching element 140 is turned on, the first reception signal generated from the first transducer 120 may be transmitted to the first receiver 130 through the first switching element 140.

The second transmitter 210 may generate and output the second transmission signal. The generated second transmission signal may be transmitted to the second transducer 220 through the second switching element 240. Each of the one or more second transmission elements included in the second transmitter 210 may transmit the second transmission signal to each of the one or more second transducer elements through the second switching element 240.

The second transmission signal may be an electrical signal. The second transmitter 210 may output the second transmission signal depending on a control signal from the controller 300. The second transmitter 210 may output the second transmission signal with the delay by the set time based on the synchronization signal having the repetition frequency. Through this, the second transmission signal may be a pulse having the repetition frequency. The second transmission signal may generally use a high voltage signal.

The second transducer 220 may convert the transmitted second transmission signal into the second ultrasonic signal. The second transducer 220 may emit the converted second ultrasonic signal to the object 10. Specifically, the second transducer 220 may emit the second ultrasonic signal to the target region inside the object 10.

The second transducer 220 may receive the second echo signal in which the emitted second ultrasonic signal is reflected from the target region inside the object 10. The second transducer 220 may generate and output a second reception signal based on the received second echo signal. The generated second reception signal may be transmitted to the second receiver 230 through the second switching element 240.

The one or more second transducer elements included in the second transducer 220 may be arranged on one surface of the second housing of the second transducer 220. Specifically, the one or more second transducer elements may be arranged in the direction parallel to the second opening so that the second ultrasonic signal and the second echo signal may be transmitted and received through the second opening provided on the one surface of the second housing.

The second receiver 230 may receive the second reception signal outputted from the second transducer 220 through the second switching element 240. The second reception signal may correspond to a low voltage signal compared to the second transmission signal, which is a high voltage signal. Therefore, in general, the second receiver 230 may use a range corresponding to a voltage of the second reception signal generated from the second transducer 220 as an input range.

Each of the one or more second reception elements may receive the second reception signal from each of the one or more second transducer elements through the second switching element 240.

The second switching element 240 may transmit the second transmission signal outputted from the second transmitter 210 to the second transducer 220. The second reception signal received from the second transducer 220 may be transmitted to the second receiver 230.

In the state in which the second switching element 240 is turned off, the second transmission signal generated from the second transmitter 210 may be transmitted to the second transducer 220 through the second switching element 240. In the state in which the second switching element 240 is turned on, the second reception signal generated from the second transducer 220 may be transmitted to the second receiver 230 through the second switching element 240.

Referring to FIGS. 11 and 12, the probe 20 of the ultrasonic imaging system 1 according to the disclosure may further include the first node N1 provided between the first transducer 120 and the first switching element 140, and the second node N2 provided between the second transducer 220 and the second switching element 240.

The signal attenuator 500 may be connected between the first node N1 and the second node N2. The signal attenuator 500 may include the at least one resistor element R. Accordingly, when a plurality of the resistance elements R is provided, a plurality of the first nodes N1 and a plurality of the second nodes N2 may be provided connected to the plurality of resistance elements (500_1, 500_2, 500_3, . . . , 500_N), respectively.

However, as illustrated in FIG. 12, the plurality of first nodes N1 connected to the plurality of first transducer elements and the plurality of second nodes N2 connected to the plurality of second transducer elements do not have to be connected in order.

For example, it may be assumed that the plurality of first nodes N1 includes N1-1, N1-2, and N1-3, the plurality of second nodes N2 includes N2-1, N2-2, and N2-3, and there is the plurality of resistance elements (500_1, 500_2, 500_3, . . . , 500_N) R_1, R_2, and R_3. Herein, as illustrated in FIG. 12, R_1 may be connected between N1-1 and N2-1, R_2 may be connected between N1-2 and N2-2, and R_3 may be connected between N1-3 and N2-3. However, R_1 may be connected between N1-2 and N2-1, R_2 may be connected between N1-1 and N2-3, and R_3 may be connected between N1-3 and N2-2. In addition, because as long as it is a connectable combination, the plurality of first nodes N1, the plurality of second nodes N2, and the plurality of resistance elements 500_1, 500_2, 500_3, . . . , 500_N may be provided in any way, the disclosure is not limited to the example of FIG. 12.

The signal attenuator 500 may attenuate the intensity of the first transmission signal outputted from the first transmitter 110. Specifically, in the state in which the first switching element 140 is turned off, the first transmission signal may be attenuated through the signal attenuator 500 and transmitted to the second switching element 240.

The signal attenuator 500 may also attenuate the intensity of the second transmission signal outputted from the second transmitter 210. Specifically, in the state in which the second switching element 240 is turned off, the second transmission signal may be attenuated through the signal attenuator 500 and transmitted to the first switching element 140.

The input device 400 may receive a signal for at least one of the first inspection mode and the second inspection mode. When the controller 300 receives signals for both the first inspection mode and the second inspection mode through the input device 400, the controller 300 may sequentially perform the first inspection mode and the second inspection mode.

A subject of input may be the user, and the user may set such that a signal for at least one of the first inspection mode and the second inspection mode is automatically inputted through the controller 300 when a specific condition is met. For example, the user may set such that a signal for the first inspection mode or the second inspection mode is inputted based on the predetermined period.

The first inspection mode may be to inspect the first operating states of the first transmitter 110 and the second receiver 230, and the second inspection mode may be to inspect the second operating states of the second transmitter 210 and the first receiver 130. The first operating states may include whether the first transmitter 110 and the second receiver 230 are operating normally, performance level, noise, etc. The second operating states may include whether the second transmitter 210 and the first receiver 130 are operating normally, performance level noise, etc.

That is, the input device 400 may obtain the command for performing at least one of the first inspection mode for inspecting the first operating states and the second inspection mode for inspecting the second operating states.

The controller 300 may control the operations of the internal components of the probe 20. The controller 300 may include at least one memory storing a program for performing the operation of the probe 20 of the ultrasonic imaging system 1 and at least one processor executing the stored program.

The memory and the processor may be implemented as separate chips. The processor may include one or more processor chips or may include one or more processing cores. The memory may include one or more memory chips or may include one or more memory blocks. The memory and the processor may also be implemented as a single chip.

The specific control operations of the controller 300 will be described later.

FIG. 13 is a flowchart illustrating a method of controlling the probe 20 of the ultrasonic imaging system 1 according to another embodiment.

Referring to FIG. 13, the controller 300 may control the input device 400 to obtain the command for performing the first inspection mode or the second inspection mode. Accordingly, a signal for the first inspection mode may be inputted to the input device 400 (1110).

The controller 300 may turn off the first switching element 140 and turn on the second switching element 240 based on the command for performing the first inspection mode obtained through the input device 400 (1120). Herein, turning off the first switching element 140 refers to operating such that the first transmitter 110 and the signal attenuator 500 are connected. Also, turning on the second switching element 240 refers to operating such that the receiver 600 and the signal attenuator 500 are connected.

The controller 300 may also control the first transmitter 110 to generate and output the first transmission signal from the first transmitter 110 based on the command for performing the first inspection mode obtained through the input device 400 (1130).

In the state in which the first switching element 140 is turned off, the first transmission signal outputted from the first transmitter 110 may be transmitted to the signal attenuator 500, and the intensity of the first transmission signal may be attenuated through the signal attenuator 500. In the state in which the second switching element 240 is turned on, the first transmission signal transmitted through the signal attenuator 500 may be transmitted to the second receiver 230. The second receiver 230 may receive the attenuated first transmission signal.

The controller 300 may control the second receiver 230 to detect the first waveform information of the received first transmission signal (1140). Specifically, the controller 300 may inspect the first operating state based on the first waveform information of the first transmission signal detected from the second receiver 230 by changing at least one of the frequency and intensity of the first transmission signal generated from the first transmitter 110. The controller 300 may also inspect the first operating state based on the first waveform information of the first transmission signal detected from the second receiver 230 by changing at least one of the gain, bandwidth, and impedance of the second receiver 230.

The controller 300 may determine whether the first operating states of the first transmitter 110 and the second receiver 230 are normal based on the first waveform information detected from the second receiver 230 (1150).

As such, the controller 300 may determine whether the first transmitter 110 and the second receiver 230 are abnormal based on the signal for the first inspection mode inputted through the input device 400.

Figure 14:
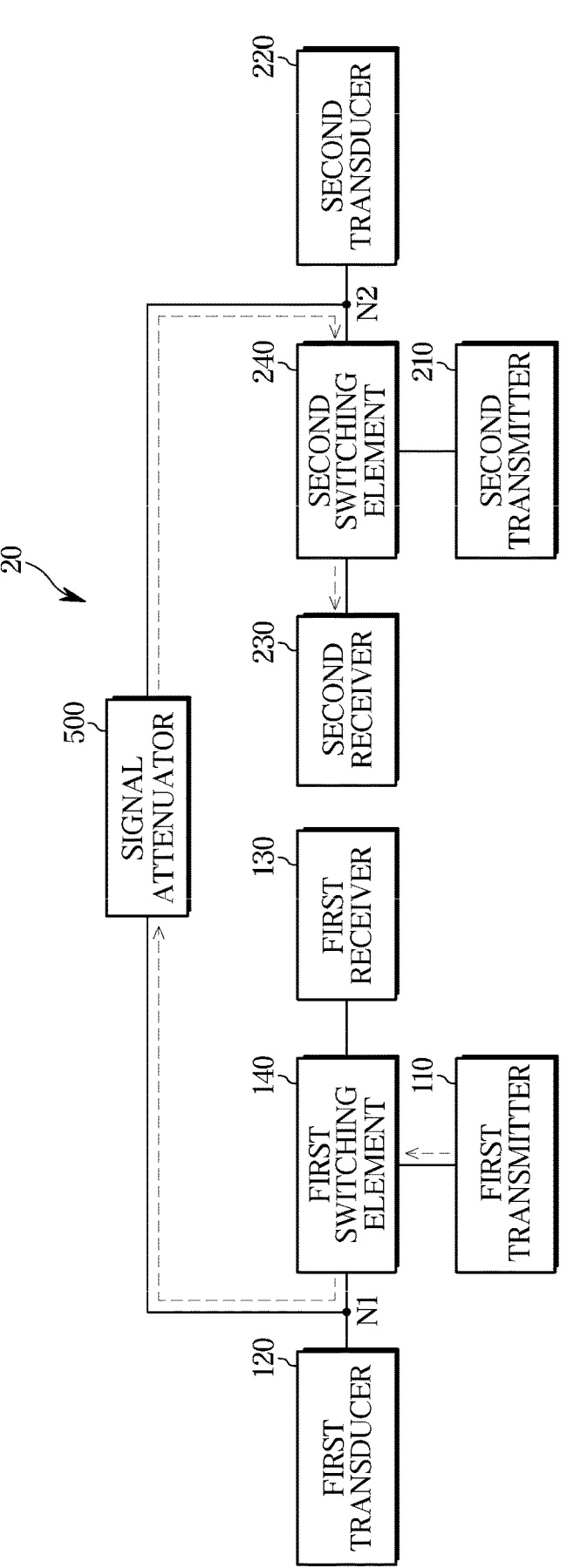
FIG. 14 is a diagram illustrating a control operation of a controller on a circuit diagram of the probe of the ultrasonic imaging system according to another embodiment.

FIG. 14 is a diagram illustrating a control operation of the controller 300 on a circuit diagram of the probe 20 of the ultrasonic imaging system 1 according to another embodiment.

Referring to FIG. 14, the controller 300 may perform a series of control operations for inspecting the first operating states of the first transmitter 110 and the second receiver 230.

The controller 300 may control the first transmitter 110 to generate the first transmission signal. The first transmission signal generated from the first transmitter 110 may be transmitted to the first switching element 140.

The controller 300 may control the first switching element 140 to be turned off based on receiving the first transmission signal. That is, the controller 300 may control the first switching element 140 such that the first transmitter 110 and the signal attenuator 500 are connected. Accordingly, the first transmission signal may be transmitted to the signal attenuator 500.

The signal attenuator 500 may attenuate the intensity of the first transmission signal, and the attenuated first transmission signal may be transmitted to the second switching element 240.

The controller 300 may control the second switching element 240 to be turned on based on receiving the attenuated first transmission signal. That is, the controller 300 may control the second switching element 240 such that the second receiver 230 and the signal attenuator 500 are connected. Accordingly, the attenuated first transmission signal may be transmitted to the second receiver 230.

Figure 15:
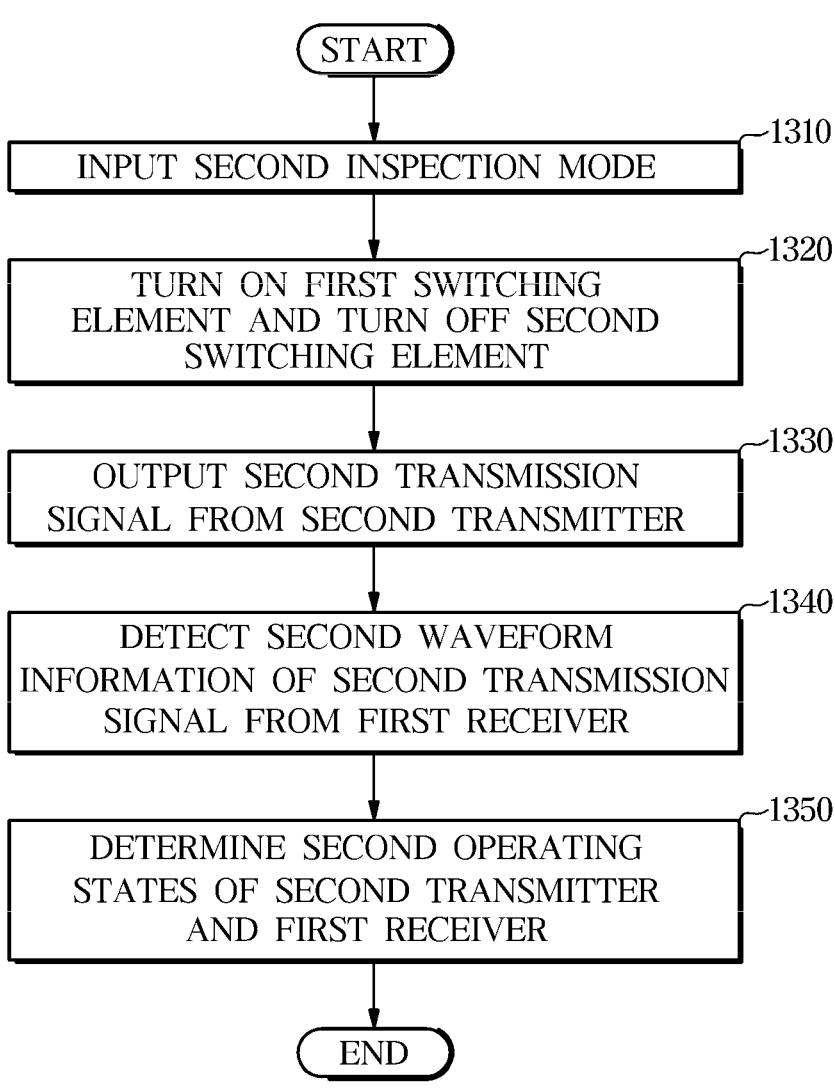
FIG. 15 is a flowchart illustrating a method of controlling the probe of the ultrasonic imaging system according to another embodiment.

FIG. 15 is a flowchart illustrating a method of controlling the probe 20 of the ultrasonic imaging system 1 according to another embodiment.

Referring to FIG. 15, the controller 300 may control the input device 400 to obtain the command for performing the first inspection mode or the second inspection mode. Accordingly, the signal for the second inspection mode may be inputted to the input device 400 (1310).

The controller 300 may turn on the first switching element 140 and turn off the second switching element 240 based on the command for performing the second inspection mode obtained through the input device 400 (1320). Herein, turning on the first switching element 140 refers to operating such that the first transmitter 110 and the signal attenuator 500 are connected. Also, turning off the second switching element 240 refers to operating such that the second transmitter 210 and the signal attenuator 500 are connected.

The controller 300 may also control the second transmitter 210 to generate and output the second transmission signal from the second transmitter 210 based on the command for performing the second inspection mode obtained through the input device 400 (1330).

In the state in which the second switching element 240 is turned off, the second transmission signal outputted from the second transmitter 210 may be transmitted to the signal attenuator 500, and the intensity of the second transmission signal may be attenuated through the signal attenuator 500. In the state in which the first switching element 140 is turned on, the second transmission signal transmitted through the signal attenuator 500 may be transmitted to the first receiver 130. The first receiver 130 may receive the attenuated second transmission signal.

The controller 300 may control the first receiver 130 to detect the second waveform information of the received second transmission signal (1340). Specifically, the controller 300 may inspect the second operating state based on the second waveform information of the second transmission signal detected from the first receiver 130 by changing at least one of the frequency and intensity of the second transmission signal generated from the second transmitter 210. The controller 300 may also inspect the second operating state based on the second waveform information of the second transmission signal detected from the first receiver 130 by changing at least one of the gain, bandwidth, and impedance of the first receiver 130.

The controller 300 may determine whether the second operating states of the second transmitter 210 and the first receiver 130 are normal based on the second waveform information detected from the first receiver 130 (1350).

As such, the controller 300 may determine whether the second transmitter 210 and the first receiver 130 are abnormal based on the signal for the second inspection mode inputted through the input device 400.

Figure 16:
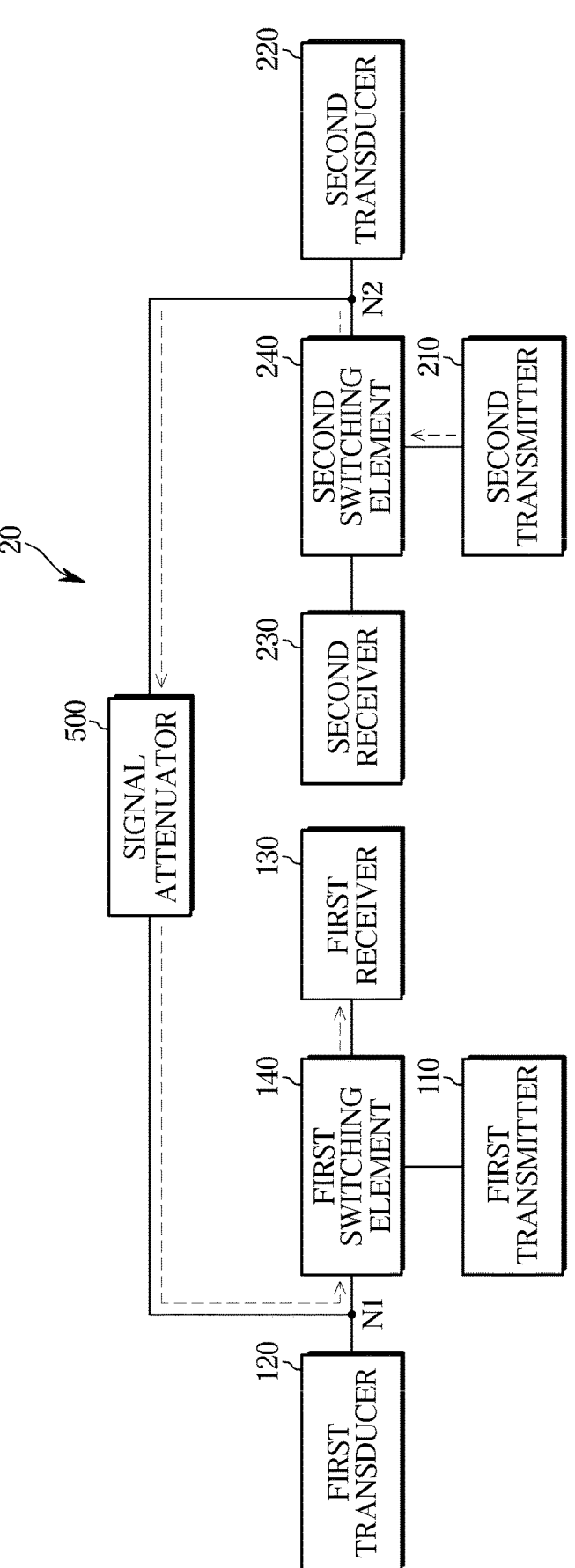
FIG. 16 is a diagram illustrating a control operation of the controller on the circuit diagram of the probe of the ultrasonic imaging system according to another embodiment.

FIG. 16 is a diagram illustrating a control operation of the controller 300 on the circuit diagram of the probe 20 of the ultrasonic imaging system 1 according to another embodiment.

Referring to FIG. 16, the controller 300 may perform a series of control operations for inspecting the second operating states of the second transmitter 210 and the first receiver 130.

The controller 300 may control the second transmitter 210 to generate the second transmission signal. The second transmission signal generated from the second transmitter 210 may be transmitted to the second switching element 240.

The controller 300 may control the second switching element 240 to be turned off based on receiving the second transmission signal. That is, the controller 300 may control the second switching element 240 such that the second transmitter 210 and the signal attenuator 500 are connected. Accordingly, the second transmission signal may be transmitted to the signal attenuator 500.

The signal attenuator 500 may attenuate the intensity of the second transmission signal, and the attenuated second transmission signal may be transmitted to the first switching element 140.

The controller 300 may control the first switching element 140 to be turned on based on receiving the attenuated second transmission signal. That is, the controller 300 may control the first switching element 140 such that the first receiver 130 and the signal attenuator 500 are connected. Accordingly, the attenuated second transmission signal may be transmitted to the first receiver 130.

Figure 17:
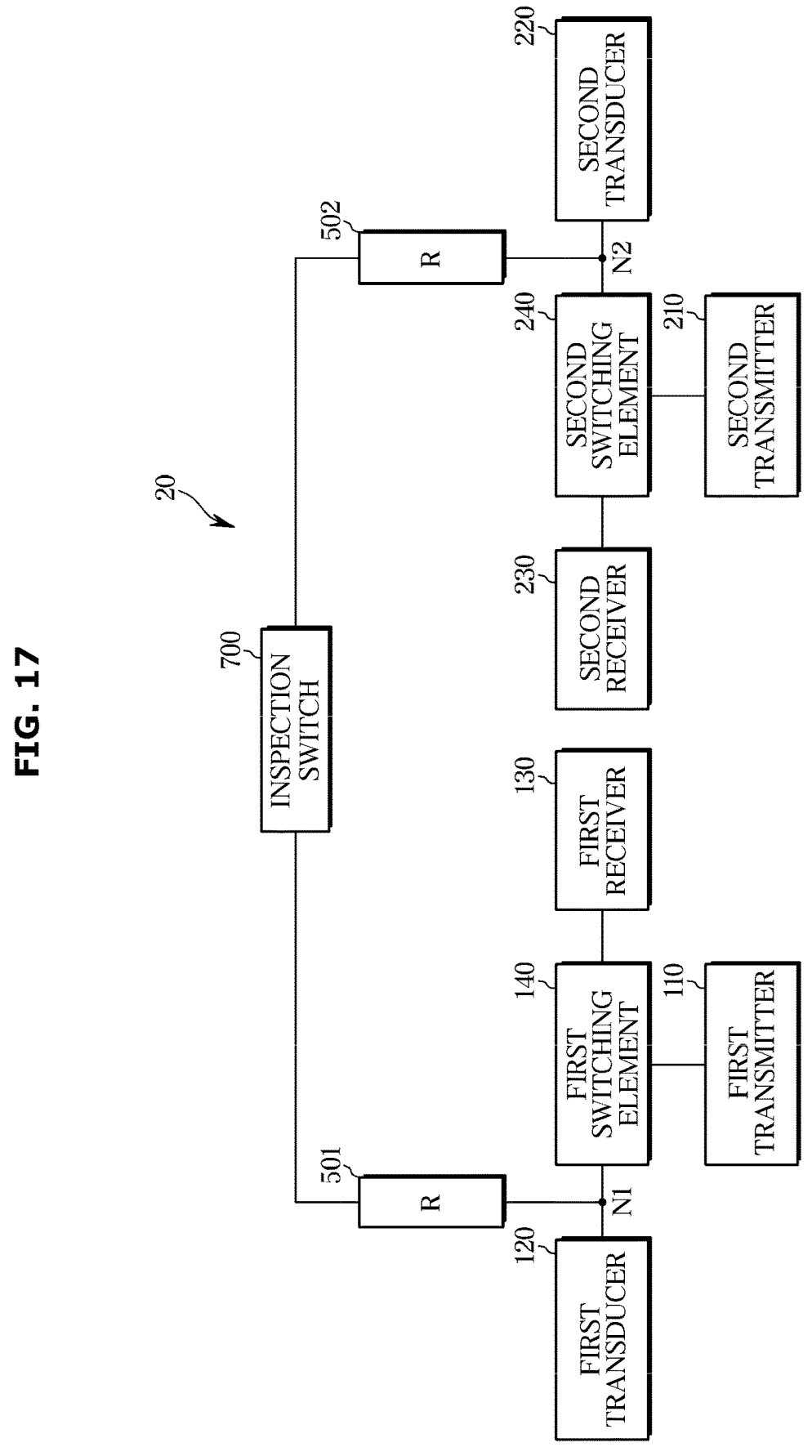
FIG. 17 is a block diagram illustrating briefly a circuit structure of the probe of the ultrasonic imaging system according to another embodiment.

FIG. 17 is a block diagram illustrating briefly a circuit structure of the probe 20 of the ultrasonic imaging system 1 according to another embodiment.

Referring to FIG. 17, the probe 20 of the ultrasonic imaging system 1 according to the disclosure may further include an inspection switch 700. The inspection switch 700 may be provided to be connected between the first node N1 and the second node N2.

The controller 300 may control the inspection switch 700 such that the transmission signal is transmitted from the first head part 100 to the second head part 200 or from the second head part 200 to the first head part 100 through the signal attenuator 500 only in the inspection mode.

Specifically, the controller 300 may close the inspection switch 700 based on the command for performing the first inspection mode or the second inspection mode obtained through the input device 400.

For example, in the first inspection mode, as the inspection switch 700 is closed, the first transmission signal may be outputted from the first transmitter 110 and attenuated through the signal attenuator 500, and may be finally transmitted to the second receiver 230. In the second inspection mode, as the inspection switch 700 is closed, the second transmission signal may be outputted from the second transmitter 210 and attenuated through the signal attenuator 500, and may be finally transmitted to the first receiver 130.

The controller 300 may keep the inspection switch 700 in an opened state when not in the inspection mode. That is, when the signal for the first inspection mode or the second inspection mode is not inputted through the input device 400, the controller 300 may open the inspection switch 700. Herein, the meaning of opening the inspection switch 700 may also include the meaning of keeping the inspection switch 700 opened.

The input device 400 may obtain a command for ending the first inspection mode or the second inspection mode. The controller 300 may open the inspection switch 700 based on the command for ending the first inspection mode or the second inspection mode obtained through the input device 400.

In the circuit structure of the probe 20 illustrated in FIG. 17, the receiver 600 independently includes the first receiver 130 and the second receiver 230 for each head, but as in the case of including the one receiver 600, the inspection switch 700 may be provided between the first node N1 and the second node N2.

In a case in which the probe 20 of the ultrasonic imaging system 1 according to the disclosure includes the receiver 600, in the first inspection mode, as the inspection switch 700 is closed, the first transmission signal may be outputted from the first transmitter 110 and attenuated through the signal attenuator 500, and may be finally transmitted to the receiver 600. In the second inspection mode, as the inspection switch 700 is closed, the second transmission signal may be outputted from the second transmitter 210 and attenuated through the signal attenuator 500, and may be finally transmitted to the receiver 600.

As described above, in a case in which the probe 20 of the ultrasonic imaging system 1 according to the disclosure includes the inspection switch 700, the signal attenuator 500 may be provided to be connected between the inspection switch 700 and the first node N1, or may be connected between the inspection switch 700 and the second node N2.

In a case in which the signal attenuator 500 includes the plurality of resistance elements (500_1, 500_2, 500_3, . . . , 500_N), for structural symmetry of the circuit, the inspection switch 700 and the plurality of resistance elements (500_1, 500_2, 500_3, . . . , 500_N) may be provided to be symmetrically connected.

For example, the probe 20 of the ultrasonic imaging system 1 according to the disclosure may include a first resistance element 501 connected between the inspection switch 700 and the first node N1, and a second resistance element 502 connected between the inspection switch 700 and the second node N2.

Figure 18:
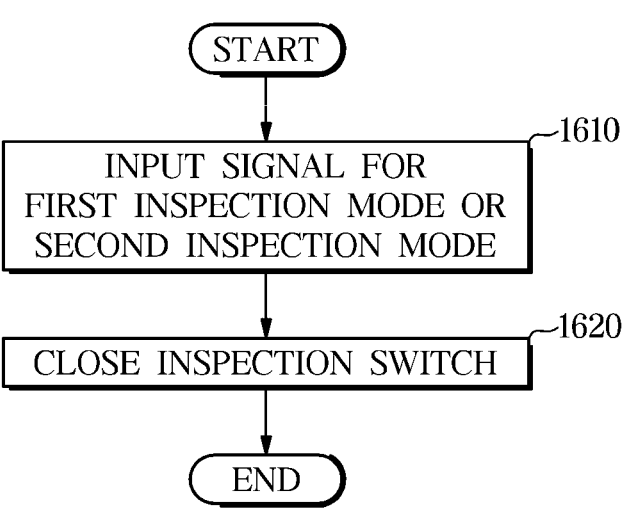
FIG. 18 is a flowchart illustrating a method of controlling the probe of the ultrasonic imaging system according to another embodiment.

FIG. 18 is a flowchart illustrating a method of controlling the probe 20 of the ultrasonic imaging system 1 according to another embodiment.

Referring to FIG. 18, the controller 300 may receive a signal for the first inspection mode or the second inspection mode through the input device 400 (1610). The controller 300 may close the inspection switch 700 based on the signal for the first inspection mode or the second inspection mode inputted (1620).

Figure 19:
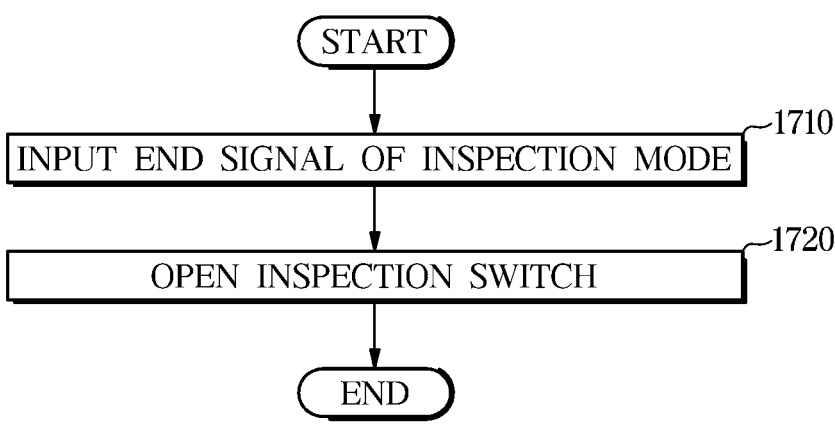
FIG. 19 is a flowchart illustrating a method of controlling the probe of the ultrasonic imaging system according to another embodiment.

FIG. 19 is a flowchart illustrating a method of controlling the probe 20 of the ultrasonic imaging system 1 according to another embodiment.

Referring to FIG. 19, the controller 300 may further receive an end signal of the inspection mode through the input device 400 (1710). Herein, the end signal of the inspection mode may include any one of an end signal of the first inspection mode and an end signal of the second inspection mode. A subject of inputting the end signal of the inspection mode may be the user, and the user may set such that the end signal of the inspection mode is automatically inputted through the controller 300 when a specific condition is met. For example, the user may set such that the end signal of the inspection mode is inputted based on a predetermined end time.

The controller 300 may open the inspection switch 700 based on the end signal of the inspection mode inputted (1720).

The probe 20 according to an embodiment may include a first transmitter 110 provided to generate a first transmission signal, a second transmitter 210 provided to generate a second transmission signal, a receiver 600 provided to receive the first transmission signal generated from the first transmitter 110 or the second transmission signal generated from the second transmitter 210, a signal attenuator 500 provided to attenuate the first transmission signal or the second transmission signal, a first switching element 140 provided to transmit the first transmission signal to the signal attenuator 500 or to transmit the second transmission signal transmitted through the signal attenuator 500 to the receiver 600, a second switching element 240 provided to transmit the second transmission signal to the signal attenuator 500 or to transmit the first transmission signal transmitted through the signal attenuator 500 to the receiver 600, a first node N1 provided between a first transducer 120 and the first switching element 140, a second node N2 provided between a second transducer 220 and the second switching element 240, and a controller 300 configured to control the first switching element 140 and the second switching element 240, wherein the signal attenuator 500 may be connected between the first node N1 and the second node N2.

The controller 300 may inspect at least one of first operating states of the first transmitter 110 and the receiver 600 and second operating states of the second transmitter 210 and the receiver 600.

The controller 300 may, in order to inspect the first operating states of the first transmitter 110 and the receiver 600, control the first switching element 140 such that the first transmitter 110 and the signal attenuator 500 are connected, and control the second switching element 240 such that the receiver 600 and the signal attenuator 500 are connected.

The controller 300 may, in order to inspect the second operating states of the second transmitter 210 and the receiver 600, control the first switching element 140 such that the receiver 600 and the signal attenuator 500 are connected, and control the second switching element 240 such that the second transmitter 210 and the signal attenuator 500 are connected.

The controller 300 may determine whether the first operating states of the first transmitter 110 and the receiver 600 are normal based on first waveform information of the first transmission signal detected by the receiver 600.

The controller 300 may determine whether the second operating states of the second transmitter 210 and the receiver 600 are normal based on second waveform information of the second transmission signal detected by the receiver 600.

The probe 20 may further include an input device 400 provided to obtain a command for performing at least one of a first inspection mode for inspecting the first operating states of the first transmitter 110 and the receiver 600 and a second inspection mode for inspecting the second operating states of the second transmitter 210 and the receiver 600.

The controller 300 may, based on the command for performing the first inspection mode obtained through the input device 400, control the first switching element 140 such that the first transmitter 110 and the signal attenuator 500 are connected, and control the second switching element 240 such that the receiver 600 and the signal attenuator 500 are connected.

The controller 300 may, based on the command for performing the second inspection mode obtained through the input device 400, control the first switching element 140 such that the receiver 600 and the signal attenuator 500 are connected, and control the second switching element 240 such that the second transmitter 210 and the signal attenuator 500 are connected.

The probe 20 may further include an inspection switch 700 connected between the first node N1 and the second node N2, wherein the controller 300 may close the inspection switch 700 based on the command for performing the first inspection mode or the second inspection mode obtained through the input device 400.

The controller 300 may open the inspection switch 700 based on a command for ending the first inspection mode or the second inspection mode obtained through the input device 400.

The receiver 600 may include a first receiver 130 provided to receive the second transmission signal generated from the second transmitter 210, and a second receiver 230 provided to receive the first transmission signal generated from the first transmitter 110, the first switching element 140 may transmit the first transmission signal to the signal attenuator 500 or transmit the second transmission signal transmitted through the signal attenuator 500 to the first receiver 130, and the second switching element 240 may transmit the second transmission signal to the signal attenuator 500 or transmit the first transmission signal transmitted through the signal attenuator 500 to the second receiver 130.

A method of controlling a probe 20 according to an embodiment may include generating a first transmission signal from a first transmitter 110, generating a second transmission signal from a second transmitter 210, attenuating the first transmission signal or the second transmission signal, receiving the first transmission signal generated from the first transmitter 110 or the second transmission signal generated from the second transmitter 210 through a receiver 600, transmitting, based on an operation of the first switching element 140, the first transmission signal to the signal attenuator 500, or the second transmission signal transmitted through the signal attenuator 500 to the receiver 600, and transmitting, based on an operation of the second switching element 240, the second transmission signal to the signal attenuator 500, or the first transmission signal transmitted through the signal attenuator 500 to the receiver 600.

The method of controlling the probe 20 may further include inspecting at least one of first operating states of the first transmitter 110 and the receiver 600 and second operating states of the second transmitter 210 and the receiver 600.

The inspecting of the first operating states may include controlling the first switching element 140 such that the first transmitter 110 and the signal attenuator 500 are connected, and controlling the second switching element 240 such that the receiver 600 and the signal attenuator 500 are connected.

The inspecting of the second operating states may include controlling the first switching element 140 such that the receiver 600 and the signal attenuator 500 are connected, and controlling the second switching element 240 such that the second transmitter 210 and the signal attenuator 500 are connected.

The inspecting of the first operating states may include determining whether the first operating states of the first transmitter 110 and the receiver 600 are normal based on first waveform information of the first transmission signal detected by the receiver 600.

The inspecting of the second operating states may include determining whether the second operating states of the second transmitter 210 and the receiver 600 are normal based on second waveform information of the second transmission signal detected by the receiver 600.

The method of controlling the probe 20 may further include obtaining, through an input device 400, a command for performing at least one of a first inspection mode for inspecting the first operating states of the first transmitter 110 and the receiver 600 and a second inspection mode for inspecting the second operating states of the second transmitter 210 and the receiver 600.

The method of controlling the probe 20 may further include, based on the command for performing the first inspection mode obtained through the input device 400, controlling the first switching element 140 such that the first transmitter 110 and the signal attenuator 500 are connected and controlling the second switching element 240 such that the receiver 600 and the signal attenuator 500 are connected.

The method of controlling the probe 20 may further include, based on the command for performing the second inspection mode obtained through the input device 400, controlling the first switching element 140 such that the receiver 600 and the signal attenuator 500 are connected and controlling the second switching element 240 such that the second transmitter 210 and the signal attenuator 500 are connected.

The method of controlling the probe 20 may further include closing an inspection switch 700 based on the command for performing the first inspection mode or the second inspection mode obtained through the input device 400.

The method of controlling the probe 20 may further include opening the inspection switch 700 based on a command for ending the first inspection mode or the second inspection mode obtained through the input device 400.

An ultrasonic imaging system 1 according to an embodiment may include a probe 20, and an ultrasonic imaging device 40 provided to communicate wirelessly with the probe 20, wherein the probe 20 may include a first transmitter 110 provided to generate a first transmission signal, a second transmitter 210 provided to generate a second transmission signal, a receiver 600 provided to receive the first transmission signal generated from the first transmitter 110 or the second transmission signal generated from the second transmitter 210, a signal attenuator 500 provided to attenuate the first transmission signal or the second transmission signal, a first switching element 140 provided to transmit the first transmission signal to the signal attenuator 500 or to transmit the second transmission signal transmitted through the signal attenuator 500 to the receiver 600, a second switching element 240 provided to transmit the second transmission signal to the signal attenuator 500 or to transmit the first transmission signal transmitted through the signal attenuator 500 to the receiver 600, a first node N1 provided between a first transducer 120 and the first switching element 140, a second node N2 provided between a second transducer 220 and the second switching element 240, and a controller 300 configured to control the first switching element 140 and the second switching element 240, and wherein the signal attenuator 500 may be connected between the first node N1 and the second node N2.

Therefore, as the signal attenuator 500 is disposed in the above structure, the signal attenuator 500 may be free from the parasitic capacitance compared to a conventional structure of being connected in parallel with the first switching element 140 or the second switching element 240, so that there is an effect that more accurate inspection is possible.

In addition, as the signal attenuators 500 are not disposed on a first head side and a second head side, respectively, and the single signal attenuator 500 connecting both the head sides is disposed, there is an effect that the number of circuit elements for self-inspection of the receiver 600 may be significantly reduced.

The disclosed embodiments may be implemented in the form of a recording medium storing instructions executable by a computer. The instructions may be stored in the form of program code, and when executed by a processor, a program module may be created to perform the operations of the disclosed embodiments.

A computer-readable recording medium may be provided in the form of a non-transitory storage medium. Herein, the 'non-transitory storage medium' simply means that it is a tangible device and does not contain signals (e.g. electromagnetic waves), and this term does not distinguish between a case where data is semi-permanently stored in a storage medium and a case where data is stored temporarily. For example, the 'non-transitory storage medium' may include a buffer where data is temporarily stored.

According to an embodiment, the methods according to various embodiments disclosed in this document may be included and provided in a computer program product. The computer program product is a commodity and may be traded between sellers and buyers. The computer program product may be distributed in the form of a machine-readable recording medium (e.g., compact disc read only memory (CD-ROM)), or may be distributed (e.g., downloaded or uploaded) online, through an application store (e.g., Play Store™) or directly between two user devices (e.g., smartphones). In the case of online distribution, at least a portion of the computer program product (e.g., a downloadable app) may be at least temporarily stored or created temporarily in the machine-readable recording medium, such as the memory of a manufacturer server, an application store server, and a relay server.

Effects that may be obtained from the disclosure are not limited to the effects mentioned above, and other effects not mentioned may be clearly understood by those skilled in the art to which the disclosure belongs from the above description.

The foregoing has illustrated and described specific embodiments. However, it should be understood by those of skilled in the art that the disclosure is not limited to the above-described embodiments, and various changes and modifications may be made without departing from the technical idea of the disclosure described in the following claims.

What is claimed is:

1. A probe comprising:

a first transmitter provided to generate a first transmission signal for obtaining an ultrasound image through a first transducer or inspecting operating states of the first transmitter and a receiver;

a second transmitter provided to generate a second transmission signal for obtaining the ultrasound image through a second transducer or inspecting operating states of the second transmitter and the receiver;

a signal attenuator provided to attenuate the first transmission signal or the second transmission signal;

the receiver provided to receive the first transmission signal through the signal attenuator, or the second transmission signal through the signal attenuator;

a first switching element provided to transmit the first transmission signal to the signal attenuator or to transmit the second transmission signal transmitted through the signal attenuator to the receiver;

a second switching element provided to transmit the second transmission signal to the signal attenuator or to transmit the first transmission signal transmitted through the signal attenuator to the receiver;

a first node provided between the first transducer and the first switching element;

a second node provided between the second transducer and the second switching element; and a controller configured to control the first switching element and the second switching element, wherein the signal attenuator is connected between the first node and the second node.

2. The probe according to claim 1, wherein the controller inspects at least one of first operating states of the first transmitter and the receiver and second operating states of the second transmitter and the receiver.

3. The probe according to claim 1, wherein the controller, in order to inspect the first operating states of the first transmitter and the receiver, controls the first switching element such that the first transmitter and the signal attenuator are connected, and controls the second switching element such that the receiver and the signal attenuator are connected.

4. The probe according to claim 1, wherein
the controller, in order to inspect the second operating states of the second transmitter and the receiver, controls the first switching element such that the receiver and the signal attenuator are connected, and controls the second switching element such that the second transmitter and the signal attenuator are connected.

5. The probe according to claim 1, wherein
the controller determines whether the first operating states of the first transmitter and the receiver are normal based on first waveform information of the first transmission signal detected by the receiver.

6. The probe according to claim 1, wherein
the controller determines whether the second operating states of the second transmitter and the receiver are normal based on second waveform information of the second transmission signal detected by the receiver.

7. The probe according to claim 1, further comprising
an input device provided to obtain a command for performing at least one of a first inspection mode for inspecting the first operating states of the first transmitter and the receiver and a second inspection mode for inspecting the second operating states of the second transmitter and the receiver.

8. The probe according to claim 7, wherein
the controller, based on the command for performing the first inspection mode obtained through the input device, controls the first switching element such that the first transmitter and the signal attenuator are connected, and controls the second switching element such that the receiver and the signal attenuator are connected.

9. The probe according to claim 7, wherein
the controller, based on the command for performing the second inspection mode obtained through the input device, controls the first switching element such that the receiver and the signal attenuator are connected, and controls the second switching element such that the second transmitter and the signal attenuator are connected.

10. The probe according to claim 7, further comprising
an inspection switch connected between the first node and the second node,
wherein the controller closes the inspection switch based on the command for performing the first inspection mode or the second inspection mode obtained through the input device.

11. The probe according to claim 10, wherein
the controller opens the inspection switch based on a command for ending the first inspection mode or the second inspection mode obtained through the input device.

12. The probe according to claim 1, wherein
the receiver comprises:
a first receiver provided to receive the second transmission signal generated from the second transmitter, and
a second receiver provided to receive the first transmission signal generated from the first transmitter,
the first switching element transmits the first transmission signal to the signal attenuator or transmit the second transmission signal transmitted through the signal attenuator to the first receiver, and
the second switching element transmits the second transmission signal to the signal attenuator or transmit the first transmission signal transmitted through the signal attenuator to the second receiver.

13. A method of controlling a probe comprising:
generating, from a first transmitter, a first transmission signal for obtaining an ultrasound image through a first transducer or inspecting operating states of the first transmitter and a receiver;
generating, from a second transmitter, a second transmission signal for obtaining the ultrasound image through a second transducer or inspecting operating states of the second transmitter and the receiver;
attenuating, by a signal attenuator, the first transmission signal or the second transmission signal;
receiving, by the receiver, the first transmission signal through the signal attenuator, or the second transmission signal through the signal attenuator;
transmitting, based on an operation of a first switching element, the first transmission signal to the signal attenuator, or the second transmission signal transmitted through the signal attenuator to the receiver; and
transmitting, based on an operation of a second switching element, the second transmission signal to the signal attenuator, or the first transmission signal transmitted through the signal attenuator to the receiver,
wherein the signal attenuator is connected between a first node between the first transducer and the first switching element and a second node between the second transducer and the second switching element.

14. The method of controlling the probe according to claim 13, further comprising
inspecting at least one of first operating states of the first transmitter and the receiver and second operating states of the second transmitter and the receiver.

15. The method of controlling the probe according to claim 14, wherein
the inspecting of the first operating states comprises:
controlling the first switching element such that the first transmitter and the signal attenuator are connected; and
controlling the second switching element such that the receiver and the signal attenuator are connected.

16. The method of controlling the probe according to claim 14, wherein
the inspecting of the second operating states comprises:
controlling the first switching element such that the receiver and the signal attenuator are connected, and
controlling the second switching element such that the second transmitter and the signal attenuator are connected.

17. The method of controlling the probe according to claim 14, wherein
the inspecting of the first operating states comprises determining whether the first operating states of the first transmitter and the receiver are normal based on first waveform information of the first transmission signal detected by the receiver.

18. The method of controlling the probe according to claim 14, wherein
the inspecting of the second operating states comprises determining whether the second operating states of the second transmitter and the receiver are normal based on second waveform information of the second transmission signal detected by the receiver.

19. The method of controlling the probe according to claim 13, further comprising
obtaining, through an input device, a command for performing at least one of a first inspection mode for inspecting the first operating states of the first transmitter and the receiver and a second inspection mode for inspecting the second operating states of the second transmitter and the receiver.

20. An ultrasonic imaging system comprising:

a probe; and an ultrasonic imaging device provided to communicate wirelessly with the probe, wherein the probe comprises:

a first transmitter provided to generate a first transmission signal for obtaining an ultrasound image through a first transducer or inspecting operating states of the first transmitter and a receiver;

a second transmitter provided to generate a second transmission signal for obtaining the ultrasound image through a second transducer or inspecting operating states of the second transmitter and the receiver;

a signal attenuator provided to attenuate the first transmission signal or the second transmission signal;

the receiver provided to receive the first transmission signal through the signal attenuator, or the second transmission signal through the signal attenuator;

a first switching element provided to transmit the first transmission signal to the signal attenuator or to transmit the second transmission signal transmitted through the signal attenuator to the receiver;

a second switching element provided to transmit the second transmission signal to the signal attenuator or to transmit the first transmission signal transmitted through the signal attenuator to the receiver;

a first node provided between the first transducer and the first switching element;

a second node provided between the second transducer and the second switching element; and a controller configured to control the first switching element and the second switching element, and wherein the signal attenuator is connected between the first node and the second node.

* * * * *